US008110192B2

(12) United States Patent  (10) Patent No.: US 8,110,192 B2
Dimitrov et al.  (45) Date of Patent: Feb. 7, 2012

(54) HUMAN IMMUNODEFICIENCY VIRUS TYPE 1 (HIV-1)-NEUTRALIZING HUMAN SINGLE-CHAIN ANTIBODIES WITH IMPROVED BREADTH AND POTENCY

(75) Inventors: Dimiter S. Dimitrov, Frederick, MD (US); Mei-Yun Zhang, Hong Kong (HK)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 188 days.

(21) Appl. No.: 12/508,913

(22) Filed: Jul. 24, 2009

(65) Prior Publication Data
US 2009/0291493 A1 Nov. 26, 2009

Related U.S. Application Data

(62) Division of application No. 10/512,966, filed as application No. PCT/US03/14095 on May 6, 2003, now Pat. No. 7,566,451.

(60) Provisional application No. 60/378,406, filed on May 6, 2002.

(51) Int. Cl.
 A61K 39/42 (2006.01)
 A61K 39/21 (2006.01)
 C07K 16/00 (2006.01)
 C12P 21/08 (2006.01)

(52) U.S. Cl. ............. 424/148.1; 424/208.1; 530/388.35; 530/387.3

(58) Field of Classification Search .................. None
See application file for complete search history.

(56) References Cited

U.S. PATENT DOCUMENTS

| 5,518,723 | A | 5/1996 | DeVico et al. |
| 5,804,440 | A | 9/1998 | Burton et al. |
| 5,925,741 | A | 7/1999 | Gershoni |
| 6,030,772 | A | 2/2000 | Devico et al. |
| 6,135,941 | A | 10/2000 | Hillman et al. |
| 6,261,558 | B1 | 7/2001 | Barbas et al. |

(Continued)

FOREIGN PATENT DOCUMENTS

EP  1 054 018 A1  11/2000
(Continued)

OTHER PUBLICATIONS

Winkler, K., et al., 2000, Changing the antigen binding specificity by single point mutations of an anti-p24 (HIV-1) antibody, J. Immunol. 165:4505-4514.*

(Continued)

*Primary Examiner* — Jeffrey S. Parkin
(74) *Attorney, Agent, or Firm* — Leydig, Voit & Mayer, Ltd.

(57) ABSTRACT

The present invention provides an antibody to human immunodeficiency virus (HIV) envelope glycoprotein that can recognize one or more strains of HIV, wherein the epitope of HIV recognized by the antibody is inducible, and wherein the antibody binding to the epitope is enhanced by the presence of CD4 and the HIV co-receptor, and related fusion proteins, conjugates, nucleic acids, vectors, host cells, compositions and methods of use to inhibit an infection of a human at risk of becoming infected with HIV, to reduce the severity of an infection of a human infected with HIV, and to treat an infection of a human with HIV.

13 Claims, 6 Drawing Sheets

```
                    1                                                   50
m9-aa_scFv  VLTQSPGTLS LSAGERATLS CRASQSVSSG SLAWYQQKPG QAPRLLIYGA
X5-aa_scFv  VLTQSPGTLS LSAGERATLS CRASQSVSSG SLAWYQQKPG QAPRLLIYGA
m6-aa_scFv  VLTQSPGTLS LSAGERATLS CRASQSVSSG SLAWYQQKPG QAPRLLIYGA 51                                                  100
m9-aa_scFv  STRATGIPDR FSGSGSGTDF TLTIGRLEPE DLAVYYCQQY GTSPYTFGQG
X5-aa_scFv  STRATGIPDR FSGSGSGTDF TLTIGRLEPE DLAVYYCQQY GTSPYTFGQG
m6-aa_scFv  STRATGIPDR FSGSGSGTDF TLTIGRLEPE DLAVYYCQQY GTSPYTFGQG 101                                                 150
m9-aa_scFv  TKLEIKRTGG GGSGGGSGG GGSVQLLEQS GAEVKKPGSS VQVSCKASGG
X5-aa_scFv  TKLEIKRTGG GGSGGGSGG GGSVQLLEQS GAEVKKPGSS VQVSCKASGG
m6-aa_scFv  TKLEIKRTGG GGSSGGASGG GGSVRLLEQS GAEVKKPGSS VQVSCKASGG 151                                                 200
m9-aa_scFv  TFSMYGFNWV RQAPGHGLEW MGGIIPIFGT TNYAQKFRGR VTFTADQATS
X5-aa_scFv  TFSMYGFNWV RQAPGHGLEW MGGIIPIFGT SNYAQKFRGR VTFTADQATS
m6-aa_scFv  TFSMYGVNWV RQAPGHGLEW MGGIIPIFGT SNYAQKFRGR VTFTADQATS 201                                                 250
m9-aa_scFv  TAYMELTNLR SDDTAVYYCA RDFGPDWEGG DSYDGSGRGF FDFWGQGTLV
X5-aa_scFv  TAYMELTNLR SDDTAVYYCA RDFGPDWEDG DSYDGSGRGF FDFWGQGTLV
m6-aa_scFv  TAYMELTNLR SDDTAVYYCA RDFGPDWEDG DSYDGSGRGF FDFWGQGTLV 251
m9-aa_scFv  NVSS (SEQ ID NO: 1)
X5-aa_scFv  TVSS (SEQ ID NO: 3)
m6-aa_scFv  TVSS (SEQ ID NO: 2)
```

U.S. PATENT DOCUMENTS

| | | | |
|---|---|---|---|
| 6,680,209 | B1 | 1/2004 | Buechler et al. |
| 7,084,257 | B2 | 8/2006 | Deshpande et al. |
| 2003/0018004 | A1 | 1/2003 | Kingsman et al. |
| 2003/0133939 | A1 | 7/2003 | Ledbetter et al. |
| 2003/0147881 | A1 | 8/2003 | Cheung et al. |
| 2004/0039172 | A1 | 2/2004 | Haynes et al. |

FOREIGN PATENT DOCUMENTS

| | | |
|---|---|---|
| WO | WO 91/00360 A1 | 1/1991 |
| WO | WO 93/15747 A1 | 8/1993 |
| WO | WO 94/07922 A1 | 4/1994 |
| WO | WO 96/15273 A1 | 5/1996 |
| WO | WO 99/24464 A1 | 5/1999 |
| WO | WO 00/40616 A1 | 7/2000 |
| WO | WO 00/55207 A1 | 9/2000 |
| WO | WO 00/69914 A2 | 11/2000 |
| WO | WO 02/093519 A2 | 11/2002 |
| WO | WO 03/033666 A2 | 4/2003 |
| WO | WO 03/092630 A2 | 11/2003 |
| WO | WO 03/095492 A1 | 11/2003 |

OTHER PUBLICATIONS

Li, Y., et al., 1996, The I binding specificity of human VH4-34 (VH4-21) encoded antibodies is determined by both VH framework region 1 and complementarity determining region 3, J. Mol. Biol. 256:577-589I.*

Brown, M., et al., 1996, Tolerance to single, but not multiple, amino acid replacements in antibody VH CDR2, J. Immunol. 156:3285-3291.*

Chen, C., et al., 1995, Enhancement and destruction of antibody function by somatic mutation: unequal occurrence is controlled by V gene combinatorial associations, The EMBO J. 14(12):2784-2794.*

Ahlborg et al., "Immune responses in congenic mice to multiple antigen peptides based on defined epitopes from the malaria antigen Pf332," *Immunology*, 88 (4), 630-635 (1996).

Barbas et al., "In vitro evolution of a neutralizing human antibody to human immunodeficiency virus type 1 to enhance affinity and broaden strain cross-reactivity," *Proc. Natl. Acad. Sci. USA*, 91 (9), 3809-3813 (1994).

Binley et al., "Human Antibody Responses to HIV Type 1 glycoprotein 41 Cloned in Phage Display Libraries Suggest Three Major Epitopes Are Recognized and Give Evidence for Conserved Antibody Motifs in Antigen Binding," *AIDS Research and Human Retroviruses*, 12 (10), 911-924 (1996).

Boots et al., "Anti-human immunodeficiency virus type 1 human monoclonal antibodies that bind discontinuous epitopes in the viral glycoproteins can identify mimotopes from recombinant phage peptide display libraries," *AIDS Res. Hum. Retrovir.*, 13 (18), 1549-1559 (1997).

Brenneman et al., "VIP and d-ala-peptide T-amide release chemokines which prevent HIV-1 GP120-induced neuronal death," *Brain Res.*, 838, 27-36 (1999).

Broliden et al., "Functional HIV-1 specific IgA antibodies in HIV-1 exposed, persistently IgG seronegative female sex workers," *Immunol. Lett.*, 79 (1-2), 29-36 (2001).

Burioni et al., "Recombinant human Fab to glycoprotein D neutralizes infectivity and prevents cell-to-cell transmission of herpes simplex viruses 1 and 2 in vitro," *Proc. Natl. Acad. Sci. USA*, 91 (4), 355-359 (1994).

Burton et al., *Science*, 266, 1024-1027 (1994).

Celada et al., *J. Exp. Med.*, 172, 1143-1150 (1990).

Chan et al., *Cell*, 93, 681-684 (1998).

Cheng et al., "Construction, Expression and Characterization of the Engineered Antibody Against Tumor Surface Antigen," *Cell Rese'arch*, 13 (1), 35-48 (2003).

Choudhry et al., "Cross-reactive HIV-1 neutralizing monoclonal antibodies selected by screening of an immune human phage library against an envelope glycoprotein (gp140) isolated from a patient (R2) with broadly HIV-1 neutralizing antibodies," *Virology*, 363 (1), 79-90 (2007).

Chow et al., "Conserved Structures Exposed in HIV-1 Envelope Glycoproteins Stabilized by Flexible Linkers as Potent Entry Inhibitors and potential Immunogens," *Biochem.*, 41, 7176-7182 (2002).

Conley et al., *PNAS*, 91, 3348-3352 (19940.

Dalgleish et al., "The CD4 (T4) Antigen is an Essential Component of the Receptor for the AIDS Retrovirus," *Nature*, 312 (5996), 763-767 (1984).

Deen et al., "A soluble form of CD4 (T4) protein inhibits AIDS virus infection," *Nature*, 331 (6151), 82-84 (1988).

Devico et al., *Virology*, 218, 258-263 (1996).

Dey et al., "Neutralization of human immunodeficiency virus type 1 by sCD4-17b, a single-chain chimeric protein, based on sequential interaction of gp120 with CD4 and coreceptor," *J. Virol.*, 77 (5), 2859-2865 (2003).

Dimitrov, *Nature Medicine*, 2(6), 640-641 (1996).

Dimitrov, *Cell*, 101, 697-702 (2000).

Dimitrov, "Virus Entry: Molecular Mechanisms and Biomedical Applications," *Nature Reviews Microbiology*, 2, 109-122 (2004).

Finnegan et al., *J. Virol.*, 76(23), 12123-12134 (2002).

Fisher et al., "HIV infection is blocked in vitro by recombinant soluble CD4," *Nature*, 331 (6151), 76-78 (1988).

Gershoni et al., *FASEB J.*, 7, 1185-1187 (1993).

Golding et al., "Increased association of glycoprotein 120-CD4 with HIV type 1 coreceptors in the presence of complex-enhanced anti-CD4 monoclonal antibodies," *AIDS Res Hum Retroviruses*, 15 (2), 149-159 (1999).

Gorny et al., "The v3 loop is accessible on the surface of most human immunodeficiency virus type 1 primary isolates and serves as a neutralization epitope," *J. Virol.*, 78 (5), 2394-2404 (2004).

Goudsmit et al., ",Human immunodeficiency virus type 1 neutralization epitope with conserved architecture elicits early type-specific antibodies in experimentally infected chimpanzees," *Proc. Natl. Acad. Sci. USA*, 85 (12), 4478-4482 (1988).

Hoogenboom et al., "Antibody Phage Display Technology and Its Applications," *Immunotechnology*, 4 (1), 1-20 (1998).

Javaherian et al., "Principal neutralizing domain of the human immunodeficiency virus type 1 envelope protein," *Proc. Natl. Acad. Sci. USA*, 86 (17), 6768-6772 (1989).

Jellis et al., "Defining critical residues in the epitope for a HIV-neutralizing monoclonal antibody using phage display and peptide array technologies," *Gene*, 137 (1), 63-68 (1993).

Kang et al., J. Virol., 68(9), 5854-5862 (1994).

Kilby et al., "Potent suppression of HIV-1 replication in humans by T-20, a peptide inhibitor of gp41-mediated virus entry," *Nat. Med.*, 4 (11), 1302-1307 (1998).

Klatzmann et al., "T-lymphocyte T4 Molecule Behaves as the Receptor for Human Retrovirus LAV," *Nature*, 312 (5996), 767-768 (1984).

Kwong et al., "Structure of an HIV gp120 envelope glycoprotein in complex with the CD4 receptor and a neutralizing human antibody," *Nature*, 393 (6686), 648-659 (1998).

Labrijn et al. "Access of Antibody Molecules to the Conserved Coreceptor Binding Site on Glycoprotein gp120 Is Sterically Restricted on Primary Human Immunodeficiency Virus Type 1," *J. Virol.*, 77 (19), 10557-10565 (2003).

Li et al., "Phage randomization in a charybdotoxin scaffold leads to CD4-mimetic recognition motifs that bind HIV-1 envelope through non-aromatic sequences," *J. Pept. Res.*, 57 (6), 507-518 (2001).

Liao et al., "Immunogenicity of constrained monoclonal antibody A32-human immunodeficiency virus (HIV) Env gp120 complexes compared to that of recombinant HIV type 1 gp120 envelope glycoproteins," *J. Virol.*, 78 (10), 5270-5278 (2004).

Lomholt et al., "Neisseria gonorrhoeae IgA1 proteases share epitopes recognized by neutralizing antibodies," *Vaccine*, 13 (13), 1213-1219 (1995).

Lacasse et al., *Science*, 283, 357-362 (1999).

Lapham et al., "Evidence for cell-surface association between fusin and the CD4-gp120 complex in human cell lines," *Science*, 274 (5287), 602-605 (1996).

Letvin et al., Immunopathogenesis and immunotherapy in AIDS virus infections, *Nat. Med.* 9(7), 861-866 (2003).

Mirzabekov et al., "Paramagnetic proteoliposomes containing a pure, native, and oriented seven-transmembrane segment protein, CCR5," *Nat. Biotech.*, 18 (6), 649-654 (2000).

Mirzabekov et al., "Enhanced expression, native purification, and characterization of CCR5, a principal HIV-1 coreceptor," *J Biological Chemistry*, 274 (40), 28745-28750 (1999).

Moore et al., "Antibody cross-competition analysis of the human immunodeficiency virus type 1 gp120 exterior envelope glycoprotein," *J. Virol.*, 70 (3), 1863-1872 (1996).

Moore et al., "Probing the Structure of the V2 Domain of Human Immunodeficiency Virus Type 1 Surface Glycoprotein gp120 with a Panel of Eight Monoclonal Antibodies: Human Immune Response to the V1 and V2 Domains," *Journal of Virology*, 67 (10), 6136-6151 (1993).

Montefiori, "Neutralizing antibodies take a swipe at HIV in vivo," *Nat. Med.*, 11(6), 593-594 (2005).

Moulard et al., *PNAS*, 99(10), 6913-6918 (2002).

Muster et al., *J. Virol.*, 67(11), 6642-6647 (1993).

Myers et al., "Targeting Immune Effector Molecules to Human Tumor Cells Through Genetic Delivery of 5T4-specific scFv Fusion Proteins," *Cancer Gene Therapy*, 9 (11), 884-896 (2002).

Palker et al., "Type-specific neutralization of the human immunodeficiency virus with antibodies to env-encoded synthetic peptides," *Proc. Natl. Acad. Sci. USA*, 85 (6), 1932-1933 (1988).

Parren et al., "Protection against HIV-1 infection in hu-PBL-SCID mice by passive immunization with a neutralizing human monoclonal antibody against the gp120 CD4-binding site," *AIDS*, 9 (6), F1-F6 (1995).

Parren et al., "Neutralization of Human Immonudeficiency Virus Type 1 by Antibody to gp120 is Determined Primarily by Occupancy of Sites on the Virion Irrespective of Epitope Specificity," *Journal of Virology*, 72 (5), 3512-3519 (1998).

Parren et al., "The Antiviral Activity of Antibodies in Vitro and in Vivo," *Advances in Immunology*, 77, 195-262 (2001).

Prabakaran et al., "Structural Mimicry of CD4 by a Cross-reactive HIV-1 Neutralizing Antibody with CDR-H2 and H3 Containing Unique Motifs," *J. Mol. Biol.*, 357, 82-89 (2006).

Sattentau et al., "Conformational Changes Induced in the Envelope Glycoproteins of the Human and Simian Immunodeficiency Viruses by Soluble Receptor Binding," *J. Virol.*,67 (12), 7383-7393 (1993).

Sattentau et al., "Conformational Changes Induced in the Human Immunodeficiency Virus Envelope Glycoprotein by Soluble CD4 Binding," *J. Exp. Med.*, 174 (2), 407-415 (1991).

Sodroski, *Cell*, 99, 243-246 (1999).

Sullivan et al., *J. Virol.*, 72(6), 4694-4703 (1998).

Ray et al., "Selection of Single Chain Variable Fragments (scFv) Against the Glycoprotein Antigen of the Rabies Virus from a Human Synthetic scFv Phage Display Library and their Fusion with the Fc Region of Human IgG1," *Clin. Exp. Immunol.* 125 (1), 94-101 (2001).

Rizzuto et al., "A Conserved HIV gp120 Glycoprotein Structure Involved in Chemokine Receptor Binding," *Science*, 280 (5371), 1949-1953 (1998).

Rizzuto et al., "Fine Definition of a Conserved CCR5-Binding Region on the Human Immunodeficiency Virus Type 1 Glycoprotein 120," *AIDS Res. Hum. Retrovir.*, 16 (8), 741-749 (2000).

Thali et al., "Characterization of Conserved Human Immunodeficiency Virus Type 1 gp120 Neutralization Epitopes Exposed upon gp120-CD4 Binding," *Journal of Virology*, 67 (7), 3978-3988 (1993).

Trkola et al., "CD-4 Dependent, Antibody-Sensitive Interactions Between HIV-1 and its Co-Receptor CCR-5," *Nature*, 384 (6605), 184-187 (1996).

Trkola et al., *J. Virol.*, 70(2), 1100-1108 (1996).

Trkola et al., "Delay of HIV-1 rebound after cessation of antiretroviral therapy through passive transfer of human neutralizing antibodies," *Nat. Med.*, 11(6), 615-622 (2005).

Ugolini et al., "Inhibition of Virus Attachment to $CD4^+$ Target Cells is a Major Mechanism of T Cell Line-adapted HIV-1 Neutralization," *J. Exp. Med.*, 186 (8), 1287-1298 (1997)).

Vogel et al., "Cross reactive anti-tetanus and anti-melittin Fab fragments by phage display after tetanus toxoid immunisation," *Hum Antibodies Hybridomas*, 7 (1), 11-20 (1996).

Winkler et al., "Changing the antgen biding specificity by single point mutations of an anti-p24 (HIV-1) antibody," *J. Immunol.*, 165, 4505-4514 (2000).

Wu et al., "CD4-Induced Interaction of Primary HIV-1 gp120 Gycoproteins with the Chemokine Receptor CCR-5," *Nature*, 384 (6605), 179-183 (1996).

Wu et al., "Multimerization of a Chimeric Anti-CD20 Single-Chain Fv-Fc Fusion Protein is Mediated Through Variable Domain Exchange," *Protein Engineering*, 14 (12), 1025-1033 (2001).

Wyatt et al. "The Antigenic Structure of the HIV gp120 Envelope Glycoprotein," *Nature*, 393 (6686), 705-711 (1998).

Wyatt et al., "Involvement of the V1/V2 Variable Loop Structure in the Exposure of Human Immunodeficiency Virus Type 1 gp120 Epitopes Induced by Receptor Binding," *Journal of Virology*, 69 (9), 5723-5733 (1995).

Wyatt et al., "The HIV-1 Envelope Glycoproteins: Fusogens, Antigens, and Immunogens," *Science*, 280 (5371), 1884-1888 (1998).

Xiang et al., "Characterization of CD4-induced epitopes on the HIV type 1 gp120 envelope glycoprotein recognized by neutralizing human monoclonal antibodies," *AIDS Res Hum Retroviruses*, 18 (16), 1207-1217 (2002).

Xiao et al., "Constitutive cell surface association between CD4 and CCR5," *Proc. Natl. Acad. Sci.*, USA 96 (13), 7496-7501 (1999).

Zhang et al., "Pharmacokinetics of Plasma Enfuvirtide After Subcutaneous Administration to Patients with Human Immunodefiency Virus: Inverse Gaussian Density Absorption and 2-compartment Disposition," *Clin. Pharmacol. Ther.*, 72 (1), 10-19 (2002).

Zhang et al., Abstract "Identification of novel broadly cross-reactive HIV neutralizing human monoclonal antibodies using alternative antigen panning (AAP) of phage display libraries," *J. Hum. Virol.*, 5 (1), 87 (2002).

Zhang et al., "Broadly cross-reactive HIV neutralizing human monoclonal antibody Fab selected by sequential antigen panning of a phage display library," *J. Immunol. Met.*, 283 (1-2), 17-25 (2003).

Zhang et al., "Identification and characterization of a new cross-reactive human immunodeficiency virus type 1-neutralizing human monoclonal antibody," *J. Virol.*, 78 (17), 9233-9242 (2004).

Zhang et al., "Improved breadth and potency of an HIV-1-neutralizing human single-chain antibody by random mutagenesis and sequential antigen panning," *J. Mol. Biol.*, 335 (1), 209-219 (2004).

Zhang et al., "Novel approaches for identification of broadly cross-reactive HIV-1 neutralizing human monoclonal antibodies and improvement of their potency," *Curr. Pharm. Des.*, 13 (2), 203-212 (2007).

Zwick et al., *J. Virol.*, 75(22), 10892-10905 (2001).

* cited by examiner

```
                 1                                                          50
m9-aa_scFv  VLTQSPGTLS  LSAGERATLS  CRASQSVSSG  SLAWYQQKPG  QAPRLLIYGA
X5-aa_scFv  VLTQSPGTLS  LSAGERATLS  CRASQSVSSG  SLAWYQQKPG  QAPRLLIYGA
m6-aa_scFv  VLTQSPGTLS  LSAGERATLS  CRASQSVSSG  SLAWYQQKPG  QAPRLLIYGA 51                                                        100
m9-aa_scFv  STRATGIPDR  FSGSGSGTDF  TLTIGRLEPE  DLAVYYCQQY  GTSPYTFGQG
X5-aa_scFv  STRATGIPDR  FSGSGSGTDF  TLTIGRLEPE  DLAVYYCQQY  GTSPYTFGQG
m6-aa_scFv  STRATGIPDR  FSGSGSGTDF  TLTIGRLEPE  DLAVYYCQQY  GTSPYTFGQG 101                                                        150
m9-aa_scFv  TKLEIKRTGG  GGSGGGGSGG  GGSVQLLEQS  GAEVKKPGSS  VQVSCKASGG
X5-aa_scFv  TKLEIKRTGG  GGSGGGGSGG  GGSVQLLEQS  GAEVKKPGSS  VQVSCKASGG
m6-aa_scFv  TKLEIKRTGG  GGSSGGASGG  GGSVRLLEQS  GAEVKKPGSS  VQVSCKASGG 151                                                        200
m9-aa_scFv  TFSMYGFNWV  RQAPGHGLEW  MGGIIPIFGT  TNYAQKFRGR  VTFTADQATS
X5-aa_scFv  TFSMYGFNWV  RQAPGHGLEW  MGGIIPIFGT  SNYAQKFRGR  VTFTADQATS
m6-aa_scFv  TFSMYGVNWV  RQAPGHGLEW  MGGIIPIFGT  SNYAQKFRGR  VTFTADQATS 201                                                        250
m9-aa_scFv  TAYMELTNLR  SDDTAVYYCA  RDFGPDWEGG  DSYDGSGRGF  FDFWGQGTLV
X5-aa_scFv  TAYMELTNLR  SDDTAVYYCA  RDFGPDWEDG  DSYDGSGRGF  FDFWGQGTLV
m6-aa_scFv  TAYMELTNLR  SDDTAVYYCA  RDFGPDWEDG  DSYDGSGRGF  FDFWGQGTLV 251
m9-aa_scFv  NVSS  (SEQ ID NO: 1)
X5-aa_scFv  TVSS  (SEQ ID NO: 3)
m6-aa_scFv  TVSS  (SEQ ID NO: 2)
```

FIGURE 2

OmpA signal                            FR1

M K K T A I A I A V A L A G F A T V A Q A A E L V L T Q S P G T L S L S A

CDR1                FR2

G E R A T L S C R A S Q S V S S G S L A W Y Q Q K P G Q A P R L L I Y G A

CDR2                     FR3

S T R A T G I P D R F S G S G S G T D F T L T I G R L E P E D L A V Y Y C Q

CDR3                   FR4

Q Y G T S P Y T F G Q G T K L E I K R T V A A P S V F I F P P S D E Q L K S

G T A S V V C L L N N F Y P R E A K V Q W K V D N A L Q S G N S Q E S V

T E H D S R D S T Y S L G S T L T L S K A D Y E K H K V Y A C E V T H Q G

L S S P V T K S F N R G E C (SEQ ID NO: 4)

FIGURE 3

| PelB Signal | FR1 |
|---|---|

M K Y L L P T A A A G L L L L A A Q P A M A E V Q L L E Q S
G A E V K K

| CDR1 | FR2 |
|---|---|

P G S S V Q V S C K A S G G T F S M Y G F N W V R Q A P G H
G L E W M G

| CDR2 | FR3 |
|---|---|

G I I P I F G T S N Y A Q K F R G R V T F T A D Q A T S T A Y
M E L T N L R

CDR3

S D D T A V Y Y C A R D F G P D W E D G D S Y D G S G R G
F F D F W G Q

FR4

G T L V T V S S A S T K G P S V F P L A P S S K S T S G G T A
A L G C L V

K D Y F P E P V T V S W N S G A L T S G V H T F P A V L Q S
S G L Y S L S

S V V T V P S S S L G T Q T Y I C N V N H K P S N T K V D K
K V E P K S C

D K T S (SEQ ID NO: 5)

FIGURE 4 atgaaccggggagtcccttttaggcacttgcttctggtgctgcaactggcgctcctcccagcagccactcagggaaagaaagt
ggtgctgggcaaaaaaggggatacagtggaactgacctgtacagcttcccagaagaagagcatacaattccactggaaaaa
ctccaaccagataaagattctgggaaatcagggctccttcttaactaaaggtccatccaagctgaatgatcgcgctgactcaag
aagaagcctttgggaccaaggaaactttcccctgatcatcaagaatcttaagatagaagactcagatacttacatctgtgaagtg
gaggaccagaaggaggaggtgcaattgctagtgttcggattgactgccaactctgacacccacctgcttcaggggcagagc
ctgaccctgaccttggagagcccccctggtagtagcccctcagtgcaatgtaggagtccaaggggtaaaaacatacagggg
gggaagaccctctccgtgtctcagctggagctccaggatagtggcacctggacatgcactgtcttgcagaaccagaagaag
gtggagttcaaaatagacatcgtggtgctagct (SEQ ID NO: 6)

1    MNRGVPFRHL LLVLQLALLP AATQGKKVVL GKKGDTVELT
     CTASQKKSIQ
51   FHWKNSNQIK ILGNQGSFLT KGPSKLNDRA DSRRSLWDQG NFPLIIKNLK
101  IEDSDTYICE VEDQKEEVQL LVFGLTANSD THLLQGQSLT LTLESPPGSS
151  PSVQCRSPRG KNIQGGKTLS VSQLELQDSG TWTCTVLQNQ
     KKVEFKIDIV
201  VLA (SEQ ID NO: 7)

FIGURE 5

VLTQSPGTLSLSAGERATLSCRASQSVSSGSLAWYQQKPGQAPRLLIYGASTRA
TGIPDRFSGSGSGTDFTLTIGRLEPEDLAVYYCQQYGTSPYTFGQGTKLEIKRTG
GGGSSGGASGGGGSVRLLEQSGAEVKKPGSSVQVSCKASGGTFSMYGVNWV
RQAPGHGLEWMGGIIPIFGTSNYAQKFRGRVTFTADQATSTAYMELTNLRSDD
TAVYYCARDFGPDWEDGDSYDGSRGFFDFWGQGTLVTVSS**GGGGSGGG
GSGGGGSGGGGSGGGGSGGGGS**MNRGVPFRHLLLVLQLALLPAATQ
GKKVVLGKKGDTVELTCTASQKKSIQFHWKNSNQIKILGNQGSFLTKGPSKLN
DRADSRRSLWDQGNFPLIIKNLKIEDSDTYICEVEDQKEEVQLLVFGLTANSDT
HLLQGQSLTLTLESPPGSSPSVQCRSPRGKNIQGGKTLSVSQLELQDSGTWTCT
VLQNQKKVEFKIDIVVLA (SEQ ID NO: 8)

FIGURE 6

SEQUENCE LISTING

```
<160> NUMBER OF SEQ ID NOS: 8

<210> SEQ ID NO 1
<211> LENGTH: 254
<212> TYPE: PRT
<213> ORGANISM: Artificial
<220> FEATURE:
<223> OTHER INFORMATION: Synthetic

<400> SEQUENCE: 1

Val Leu Thr Gln Ser Pro Gly Thr Leu Ser Leu Ser Ala Gly Glu Arg
1               5                   10                  15

Ala Thr Leu Ser Cys Arg Ala Ser Gln Ser Val Ser Ser Gly Ser Leu
            20                  25                  30

Ala Trp Tyr Gln Gln Lys Pro Gly Gln Ala Pro Arg Leu Leu Ile Tyr
        35                  40                  45

Gly Ala Ser Thr Arg Ala Thr Gly Ile Pro Asp Arg Phe Ser Gly Ser
    50                  55                  60

Gly Ser Gly Thr Asp Phe Thr Leu Thr Ile Gly Arg Leu Glu Pro Glu
65                  70                  75                  80

Asp Leu Ala Val Tyr Tyr Cys Gln Gln Tyr Gly Thr Ser Pro Tyr Thr
                85                  90                  95

Phe Gly Gln Gly Thr Lys Leu Glu Ile Lys Arg Thr Gly Gly Gly Gly
            100                 105                 110

Ser Gly Gly Gly Gly Ser Gly Gly Gly Ser Val Gln Leu Leu Glu
            115                 120                 125

Gln Ser Gly Ala Glu Val Lys Lys Pro Gly Ser Ser Val Gln Val Ser
    130                 135                 140

Cys Lys Ala Ser Gly Gly Thr Phe Ser Met Tyr Gly Phe Asn Trp Val
145                 150                 155                 160

Arg Gln Ala Pro Gly His Gly Leu Glu Trp Met Gly Gly Ile Ile Pro
                165                 170                 175

Ile Phe Gly Thr Thr Asn Tyr Ala Gln Lys Phe Arg Gly Arg Val Thr
            180                 185                 190

Phe Thr Ala Asp Gln Ala Thr Ser Thr Ala Tyr Met Glu Leu Thr Asn
        195                 200                 205

Leu Arg Ser Asp Asp Thr Ala Val Tyr Tyr Cys Ala Arg Asp Phe Gly
    210                 215                 220

Pro Asp Trp Glu Gly Gly Asp Ser Tyr Asp Gly Ser Gly Arg Gly Phe
225                 230                 235                 240

Phe Asp Phe Trp Gly Gln Gly Thr Leu Val Asn Val Ser Ser
                245                 250
```

245                 250

<210> SEQ ID NO 2
<211> LENGTH: 254
<212> TYPE: PRT
<213> ORGANISM: Artificial
<220> FEATURE:
<223> OTHER INFORMATION: Synthetic

<400> SEQUENCE: 2

Val Leu Thr Gln Ser Pro Gly Thr Leu Ser Leu Ser Ala Gly Glu Arg
1               5                   10                  15

Ala Thr Leu Ser Cys Arg Ala Ser Gln Ser Val Ser Ser Gly Ser Leu
            20                  25                  30

Ala Trp Tyr Gln Gln Lys Pro Gly Gln Ala Pro Arg Leu Leu Ile Tyr
        35                  40                  45

Gly Ala Ser Thr Arg Ala Thr Gly Ile Pro Asp Arg Phe Ser Gly Ser
    50                  55                  60

Gly Ser Gly Thr Asp Phe Thr Leu Thr Ile Gly Arg Leu Glu Pro Glu
65                  70                  75                  80

Asp Leu Ala Val Tyr Tyr Cys Gln Gln Tyr Gly Thr Ser Pro Tyr Thr
                85                  90                  95

Phe Gly Gln Gly Thr Lys Leu Glu Ile Lys Arg Thr Gly Gly Gly Gly
            100                 105                 110

Ser Ser Gly Gly Ala Ser Gly Gly Gly Ser Val Arg Leu Leu Glu
        115                 120                 125

Gln Ser Gly Ala Glu Val Lys Lys Pro Gly Ser Ser Val Gln Val Ser
    130                 135                 140

Cys Lys Ala Ser Gly Gly Thr Phe Ser Met Tyr Gly Val Asn Trp Val
145                 150                 155                 160

Arg Gln Ala Pro Gly His Gly Leu Glu Trp Met Gly Gly Ile Ile Pro
                165                 170                 175

Ile Phe Gly Thr Ser Asn Tyr Ala Gln Lys Phe Arg Gly Arg Val Thr
            180                 185                 190

Phe Thr Ala Asp Gln Ala Thr Ser Thr Ala Tyr Met Glu Leu Thr Asn
        195                 200                 205

Leu Arg Ser Asp Asp Thr Ala Val Tyr Tyr Cys Ala Arg Asp Phe Gly
    210                 215                 220

Pro Asp Trp Glu Asp Gly Asp Ser Tyr Asp Gly Ser Gly Arg Gly Phe
225                 230                 235                 240

Phe Asp Phe Trp Gly Gln Gly Thr Leu Val Thr Val Ser Ser
                245                 250

<210> SEQ ID NO 3
<211> LENGTH: 254
<212> TYPE: PRT
<213> ORGANISM: Artificial
<220> FEATURE:
<223> OTHER INFORMATION: Synthetic

<400> SEQUENCE: 3

Val Leu Thr Gln Ser Pro Gly Thr Leu Ser Leu Ser Ala Gly Glu Arg
1               5                   10                  15

Ala Thr Leu Ser Cys Arg Ala Ser Gln Ser Val Ser Ser Gly Ser Leu
            20                  25                  30

Ala Trp Tyr Gln Gln Lys Pro Gly Gln Ala Pro Arg Leu Leu Ile Tyr
        35                  40                  45

Gly Ala Ser Thr Arg Ala Thr Gly Ile Pro Asp Arg Phe Ser Gly Ser

```
            50                  55                  60
Gly Ser Gly Thr Asp Phe Thr Leu Thr Ile Gly Arg Leu Glu Pro Glu
 65                  70                  75                  80

Asp Leu Ala Val Tyr Tyr Cys Gln Gln Tyr Gly Thr Ser Pro Tyr Thr
                 85                  90                  95

Phe Gly Gln Gly Thr Lys Leu Glu Ile Lys Arg Thr Gly Gly Gly Gly
            100                 105                 110

Ser Gly Gly Gly Gly Ser Gly Gly Gly Ser Val Gln Leu Glu
            115                 120                 125

Gln Ser Gly Ala Glu Val Lys Lys Pro Gly Ser Val Gln Val Ser
130                 135                 140

Cys Lys Ala Ser Gly Gly Thr Phe Ser Met Tyr Gly Phe Asn Trp Val
145                 150                 155                 160

Arg Gln Ala Pro Gly His Gly Leu Glu Trp Met Gly Gly Ile Ile Pro
                165                 170                 175

Ile Phe Gly Thr Ser Asn Tyr Ala Gln Lys Phe Arg Gly Arg Val Thr
            180                 185                 190

Phe Thr Ala Asp Gln Ala Thr Ser Thr Ala Tyr Met Glu Leu Thr Asn
            195                 200                 205

Leu Arg Ser Asp Asp Thr Ala Val Tyr Tyr Cys Ala Arg Asp Phe Gly
210                 215                 220

Pro Asp Trp Glu Asp Gly Asp Ser Tyr Asp Gly Ser Arg Gly Phe
225                 230                 235                 240

Phe Asp Phe Trp Gly Gln Gly Thr Leu Val Thr Val Ser Ser
                245                 250

<210> SEQ ID NO 4
<211> LENGTH: 237
<212> TYPE: PRT
<213> ORGANISM: Artificial
<220> FEATURE:
<223> OTHER INFORMATION: Synthetic

<400> SEQUENCE: 4

Met Lys Lys Thr Ala Ile Ala Ile Ala Val Ala Leu Ala Gly Phe Ala
 1               5                   10                  15

Thr Val Ala Gln Ala Ala Glu Leu Val Leu Thr Gln Ser Pro Gly Thr
            20                  25                  30

Leu Ser Leu Ser Ala Gly Glu Arg Ala Thr Leu Ser Cys Arg Ala Ser
        35                  40                  45

Gln Ser Val Ser Ser Gly Ser Leu Ala Trp Tyr Gln Gln Lys Pro Gly
50                  55                  60

Gln Ala Pro Arg Leu Leu Ile Tyr Gly Ala Ser Thr Arg Ala Thr Gly
 65                  70                  75                  80

Ile Pro Asp Arg Phe Ser Gly Ser Gly Ser Gly Thr Asp Phe Thr Leu
                 85                  90                  95

Thr Ile Gly Arg Leu Glu Pro Glu Asp Leu Ala Val Tyr Tyr Cys Gln
            100                 105                 110

Gln Tyr Gly Thr Ser Pro Tyr Thr Phe Gly Gln Gly Thr Lys Leu Glu
            115                 120                 125

Ile Lys Arg Thr Val Ala Ala Pro Ser Val Phe Ile Phe Pro Pro Ser
130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175
```

Leu Gln Ser Gly Asn Ser Gln Glu Ser Val Thr Glu His Asp Ser Arg
            180                 185                 190

Asp Ser Thr Tyr Ser Leu Gly Ser Thr Leu Thr Leu Ser Lys Ala Asp
        195                 200                 205

Tyr Glu Lys His Lys Val Tyr Ala Cys Glu Val Thr His Gln Gly Leu
210                 215                 220

Ser Ser Pro Val Thr Lys Ser Phe Asn Arg Gly Glu Cys
225                 230                 235

<210> SEQ ID NO 5
<211> LENGTH: 261
<212> TYPE: PRT
<213> ORGANISM: Artificial
<220> FEATURE:
<223> OTHER INFORMATION: Synthetic

<400> SEQUENCE: 5

Met Lys Tyr Leu Leu Pro Thr Ala Ala Ala Gly Leu Leu Leu Leu Ala
1               5                   10                  15

Ala Gln Pro Ala Met Ala Glu Val Gln Leu Leu Glu Gln Ser Gly Ala
            20                  25                  30

Glu Val Lys Lys Pro Gly Ser Ser Val Gln Val Ser Cys Lys Ala Ser
        35                  40                  45

Gly Gly Thr Phe Ser Met Tyr Gly Phe Asn Trp Val Arg Gln Ala Pro
    50                  55                  60

Gly His Gly Leu Glu Trp Met Gly Gly Ile Ile Pro Ile Phe Gly Thr
65                  70                  75                  80

Ser Asn Tyr Ala Gln Lys Phe Arg Gly Arg Val Thr Phe Thr Ala Asp
                85                  90                  95

Gln Ala Thr Ser Thr Ala Tyr Met Glu Leu Thr Asn Leu Arg Ser Asp
            100                 105                 110

Asp Thr Ala Val Tyr Tyr Cys Ala Arg Asp Phe Gly Pro Asp Trp Glu
        115                 120                 125

Asp Gly Asp Ser Tyr Asp Gly Ser Gly Arg Gly Phe Phe Asp Phe Trp
    130                 135                 140

Gly Gln Gly Thr Leu Val Thr Val Ser Ser Ala Ser Thr Lys Gly Pro
145                 150                 155                 160

Ser Val Phe Pro Leu Ala Pro Ser Ser Lys Ser Thr Ser Gly Gly Thr
                165                 170                 175

Ala Ala Leu Gly Cys Leu Val Lys Asp Tyr Phe Pro Glu Pro Val Thr
            180                 185                 190

Val Ser Trp Asn Ser Gly Ala Leu Thr Ser Gly Val His Thr Phe Pro
        195                 200                 205

Ala Val Leu Gln Ser Ser Gly Leu Tyr Ser Leu Ser Ser Val Val Thr
    210                 215                 220

Val Pro Ser Ser Ser Leu Gly Thr Gln Thr Tyr Ile Cys Asn Val Asn
225                 230                 235                 240

His Lys Pro Ser Asn Thr Lys Val Asp Lys Lys Val Glu Pro Lys Ser
                245                 250                 255

Cys Asp Lys Thr Ser
            260

<210> SEQ ID NO 6
<211> LENGTH: 609
<212> TYPE: DNA
<213> ORGANISM: Artificial
<220> FEATURE:

<223> OTHER INFORMATION: Synthetic

<400> SEQUENCE: 6

```
atgaaccggg gagtcccttt taggcacttg cttctggtgc tgcaactggc gctcctccca      60
gcagccactc agggaaagaa agtggtgctg ggcaaaaaag gggatacagt ggaactgacc     120
tgtacagctt cccagaagaa gagcatacaa ttccactgga aaaactccaa ccagataaag     180
attctgggaa atcagggctc cttcttaact aaaggtccat ccaagctgaa tgatcgcgct     240
gactcaagaa gaagcctttg ggaccaagga aactttcccc tgatcatcaa gaatcttaag     300
atagaagact cagatactta catctgtgaa gtggaggacc agaaggagga ggtgcaattg     360
ctagtgttcg gattgactgc caactctgac acccacctgc ttcagggca  gagcctgacc     420
ctgaccttgg agagcccccc tggtagtagc ccctcagtgc aatgtaggag tccaaggggt     480
aaaaacatac agggggggaa gaccctctcc gtgtctcagc tggagctcca ggatagtggc     540
acctggacat gcactgtctt gcagaaccag aagaaggtgg agttcaaaat agacatcgtg     600
gtgctagct                                                             609
```

<210> SEQ ID NO 7
<211> LENGTH: 203
<212> TYPE: PRT
<213> ORGANISM: Artificial
<220> FEATURE:
<223> OTHER INFORMATION: Synthetic

<400> SEQUENCE: 7

```
Met Asn Arg Gly Val Pro Phe Arg His Leu Leu Leu Val Leu Gln Leu
1               5                   10                  15
Ala Leu Leu Pro Ala Ala Thr Gln Gly Lys Lys Val Val Leu Gly Lys
            20                  25                  30
Lys Gly Asp Thr Val Glu Leu Thr Cys Thr Ala Ser Gln Lys Lys Ser
        35                  40                  45
Ile Gln Phe His Trp Lys Asn Ser Asn Gln Ile Lys Ile Leu Gly Asn
    50                  55                  60
Gln Gly Ser Phe Leu Thr Lys Gly Pro Ser Lys Leu Asn Asp Arg Ala
65                  70                  75                  80
Asp Ser Arg Arg Ser Leu Trp Asp Gln Gly Asn Phe Pro Leu Ile Ile
                85                  90                  95
Lys Asn Leu Lys Ile Glu Asp Ser Asp Thr Tyr Ile Cys Glu Val Glu
            100                 105                 110
Asp Gln Lys Glu Glu Val Gln Leu Leu Val Phe Gly Leu Thr Ala Asn
        115                 120                 125
Ser Asp Thr His Leu Leu Gln Gly Gln Ser Leu Thr Leu Thr Leu Glu
    130                 135                 140
Ser Pro Pro Gly Ser Ser Pro Ser Val Gln Cys Arg Ser Pro Arg Gly
145                 150                 155                 160
Lys Asn Ile Gln Gly Gly Lys Thr Leu Ser Val Ser Gln Leu Glu Leu
                165                 170                 175
Gln Asp Ser Gly Thr Trp Thr Cys Thr Val Leu Gln Asn Gln Lys Lys
            180                 185                 190
Val Glu Phe Lys Ile Asp Ile Val Val Leu Ala
        195                 200
```

<210> SEQ ID NO 8
<211> LENGTH: 487
<212> TYPE: PRT
<213> ORGANISM: Artificial

-continued

```
<220> FEATURE:
<223> OTHER INFORMATION: Synthetic

<400> SEQUENCE: 8

Val Leu Thr Gln Ser Pro Gly Thr Leu Ser Leu Ser Ala Gly Glu Arg
1               5                   10                  15

Ala Thr Leu Ser Cys Arg Ala Ser Gln Ser Val Ser Ser Gly Ser Leu
            20                  25                  30

Ala Trp Tyr Gln Gln Lys Pro Gly Gln Ala Pro Arg Leu Leu Ile Tyr
        35                  40                  45

Gly Ala Ser Thr Arg Ala Thr Gly Ile Pro Asp Arg Phe Ser Gly Ser
    50                  55                  60

Gly Ser Gly Thr Asp Phe Thr Leu Thr Ile Gly Arg Leu Glu Pro Glu
65                  70                  75                  80

Asp Leu Ala Val Tyr Tyr Cys Gln Gln Tyr Gly Thr Ser Pro Tyr Thr
                85                  90                  95

Phe Gly Gln Gly Thr Lys Leu Glu Ile Lys Arg Thr Gly Gly Gly Gly
            100                 105                 110

Ser Ser Gly Gly Ala Ser Gly Gly Gly Ser Val Arg Leu Leu Glu
            115                 120                 125

Gln Ser Gly Ala Glu Val Lys Lys Pro Gly Ser Ser Val Gln Val Ser
    130                 135                 140

Cys Lys Ala Ser Gly Gly Thr Phe Ser Met Tyr Gly Val Asn Trp Val
145                 150                 155                 160

Arg Gln Ala Pro Gly His Gly Leu Glu Trp Met Gly Gly Ile Ile Pro
                165                 170                 175

Ile Phe Gly Thr Ser Asn Tyr Ala Gln Lys Phe Arg Gly Arg Val Thr
            180                 185                 190

Phe Thr Ala Asp Gln Ala Thr Ser Thr Ala Tyr Met Glu Leu Thr Asn
        195                 200                 205

Leu Arg Ser Asp Asp Thr Ala Val Tyr Tyr Cys Ala Arg Asp Phe Gly
    210                 215                 220

Pro Asp Trp Glu Asp Gly Asp Ser Tyr Asp Gly Ser Gly Arg Gly Phe
225                 230                 235                 240

Phe Asp Phe Trp Gly Gln Gly Thr Leu Val Thr Val Ser Ser Gly Gly
                245                 250                 255

Gly Gly Ser Gly Gly Gly Ser Gly Gly Gly Ser Gly Gly
            260                 265                 270

Gly Ser Gly Gly Gly Gly Ser Gly Gly Gly Ser Met Asn Arg Gly
        275                 280                 285

Val Pro Phe Arg His Leu Leu Leu Val Leu Gln Leu Ala Leu Leu Pro
    290                 295                 300

Ala Ala Thr Gln Gly Lys Lys Val Val Leu Gly Lys Lys Gly Asp Thr
305                 310                 315                 320

Val Glu Leu Thr Cys Thr Ala Ser Gln Lys Lys Ser Ile Gln Phe His
                325                 330                 335

Trp Lys Asn Ser Asn Gln Ile Lys Ile Leu Gly Asn Gln Gly Ser Phe
            340                 345                 350

Leu Thr Lys Gly Pro Ser Lys Leu Asn Asp Arg Ala Asp Ser Arg Arg
        355                 360                 365

Ser Leu Trp Asp Gln Gly Asn Phe Pro Leu Ile Ile Lys Asn Leu Lys
    370                 375                 380

Ile Glu Asp Ser Asp Thr Tyr Ile Cys Glu Val Glu Asp Gln Lys Glu
385                 390                 395                 400
```

-continued

```
Glu Val Gln Leu Leu Val Phe Gly Leu Thr Ala Asn Ser Asp Thr His
                405                 410                 415

Leu Leu Gln Gly Gln Ser Leu Thr Leu Thr Leu Glu Ser Pro Pro Gly
            420                 425                 430

Ser Ser Pro Ser Val Gln Cys Arg Ser Pro Arg Gly Lys Asn Ile Gln
        435                 440                 445

Gly Gly Lys Thr Leu Ser Val Ser Gln Leu Glu Leu Gln Asp Ser Gly
    450                 455                 460

Thr Trp Thr Cys Thr Val Leu Gln Asn Gln Lys Lys Val Glu Phe Lys
465                 470                 475                 480

Ile Asp Ile Val Val Leu Ala
                485
```

HUMAN IMMUNODEFICIENCY VIRUS TYPE 1 (HIV-1)-NEUTRALIZING HUMAN SINGLE-CHAIN ANTIBODIES WITH IMPROVED BREADTH AND POTENCY

This patent application is a divisional of U.S. patent application No. 10/512,966, filed Dec. 15, 2004, now U.S. Pat. No. 7,566,451, which is a U.S. National Phase of International Patent Application No. PCT/US03/14095, filed May 6, 2003, which claims the benefit of U.S. Provisional Patent Application No. 60/378,406, filed May 6, 2002, which are incorporated by reference.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 18,600 Byte ASCII (Text) file named "705193ST25.TXT," created on Jul. 14, 2009.

TECHNICAL FIELD OF THE INVENTION

The present invention relates to antibodies, in particular monoclonal antibodies, specifically cross-reactive human immunodeficiency virus (HIV) neutralizing antibodies, and related fusion proteins, conjugates, nucleic acids, vectors, host cells, compositions, and methods of use.

BACKGROUND OF THE INVENTION

Binding of the HIV-1 envelope glycoprotein (Env, gp120-gp41) to CD4 and coreceptors initiates a series of conformational changes that are the heart of the fusion machinery leading to viral entry[1]. The elucidation of the nature of the Env conformational changes is not only a clue to the mechanism of HIV type 1 (HIV-1) entry but may also provide new tools for the development of inhibitors and vaccines.[2,3] It has been proposed that the interaction of coreceptor molecules with the Env-CD4 complex leads to intermediate Env conformations that may include structures conserved among various HIV 1 isolates that could be used as vaccines[4,5]. Of the four known potent broadly neutralizing antibodies (b12[7], 2F5[8,9], 2G12[10,] and 4E10/Z13[11]), none has a receptor-inducible epitope.

No single broadly cross-reactive monoclonal antibody with potent neutralization activity for all primary HIV isolates has been isolated and characterized. Typically, monoclonal antibodies against CD4-inducible epitopes, such as 17b and CG10, are only weakly neutralizing against primary isolates[16], suggesting that CD4-inducible epitopes on gp120 may not serve as targets for potent broadly neutralizing antibodies.

It is an object of the present invention to provide antibodies to receptor-inducible epitopes, wherein the antibodies exhibit high affinity of binding of HIV and neutralizing activity. The antibodies can be used, alone or in combination with other active agents or as fusion proteins or conjugates with other active agents, to inhibit HIV and as tools to dissect mechanisms of HIV cellular entry. This and other objects and advantages of the present invention, as well as additional inventive features, will become apparent from the detailed description provided herein.

BRIEF SUMMARY OF THE INVENTION

The present invention provides an isolated or purified nucleic acid molecule comprising the nucleotide sequence encoding the amino acid sequence of SEQ ID NO: 1, SEQ ID NO: 2, SEQ ID NO: 8 or a variant of any of the foregoing, wherein the variant retains the ability to bind to the same epitope as that of SEQ ID NO: 1, 2 or 8 respectively, to a greater or lesser extent. Also provided are a vector comprising such a nucleic acid molecule, a composition comprising the nucleic acid molecule, optionally in the form of a vector, and a host cell comprising the nucleic acid molecule, optionally in the form of a vector.

The present invention further provides an antibody to HIV envelope glycoprotein that can recognize one or more strains of HIV, wherein the epitope of HIV recognized by the antibody is inducible, and wherein the antibody binding to the epitope is enhanced by the presence of CD4 and the HIV co-receptor. Also provided are a composition comprising the antibody, a fusion protein or conjugate comprising the antibody, and a composition comprising the fusion protein or conjugate.

The present invention still further provides methods of using the above nucleic acid molecules, vectors, host cells, antibodies, fusion proteins and conjugates. In one embodiment, the present invention provides a method of inhibiting an infection of a human at risk of becoming infected with HIV. In another embodiment, the present invention provides a method of reducing the severity of an infection of a human infected with HIV. In yet another embodiment, the present invention provides a method of treating an infection of a human with HIV. The methods comprise administering to the human an isolated or purified nucleic acid molecule encoding an above-described antibody; optionally as part of a fusion protein, wherein the nucleic acid molecule is optionally in the form of a vector and/or optionally contained within a cell, or the antibody, itself, optionally as part of a fusion protein or conjugate.

BRIEF DESCRIPTION OF THE FIGURES

FIG. 2 is the scFv amino acid sequence alignment, in which the mutated amino acids are indicated in bold (SEQ ID NOS: 1-3).

FIG. 3 is the amino acid sequence of the X5 light chain (SEQ ID NO: 4).

FIG. 4 is the amino acid sequence of the X5 heavy chain (SEQ ID NO: 5).

FIG. 5 is the DNA (SEQ ID NO: 6) and amino acid (SEQ ID NO: 7) sequences of domain 2 of CD4.

FIG. 6 is the amino acid sequence of an ScFv-CD4 fusion protein comprising from the amino terminus to the carboxy terminus (read from left to right and top to bottom) m6, linker and domain 2 of CD4 (SEQ ID NO: 8).

DETAILED DESCRIPTION OF THE PRESENT INVENTION

Figure 1:
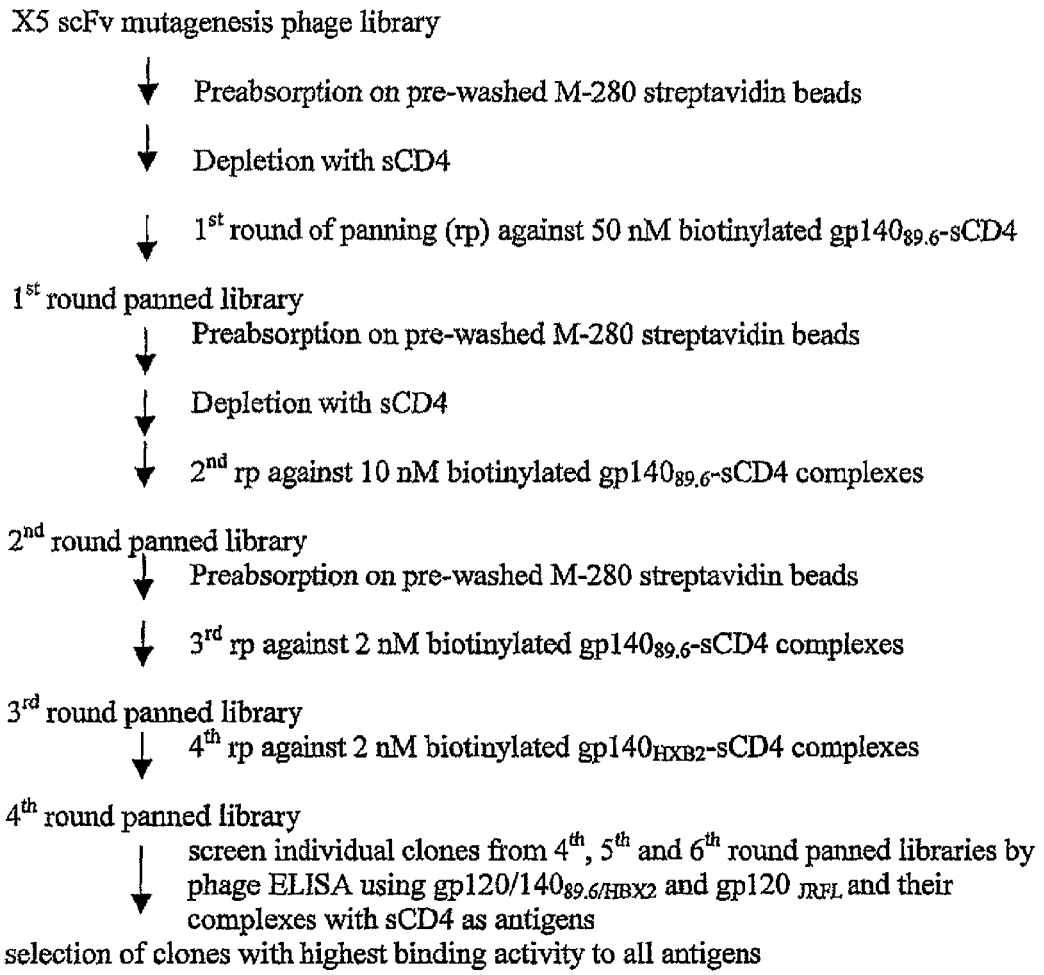
FIG. 1 is a flow chart of sequential panning (m6 and m9).

The present invention may be understood more readily by reference to the following detailed description of preferred embodiments of the invention and the Examples included therein and to the Figures and their previous and following description.

Before the present compounds, compositions, and/or methods are disclosed and described, it is to be understood that this invention is not limited to specific synthetic methods, specific recombinant biotechnology methods unless otherwise specified, or to particular reagents, pharmaceutical formulations or administration regimens unless otherwise specified, as such may, of course, vary. It is also to be understood that the terminology used herein is for the purpose of describing particular embodiments only and is not intended to be limiting.

It must be noted that, as used in the specification and the appended claims, the singular forms "a," "an" and "the" can include plural referents unless the context clearly dictates otherwise. Thus, for example, reference to "a compound" includes mixtures of compounds, reference to "a pharmaceutical carrier" includes mixtures of two or more such carriers, and the like.

In this specification and in the claims which follow, reference will be made to a number of terms, which shall be defined to have the following meanings:

Herein the term "sequential antigen panning" refers to a method of producing an antibody or antibodies comprising isolating the antibody or antibodies by screening a phage display library for antibodies that can bind to an antigen, wherein the isolation is continued by screening the binding antibodies for the ability to bind the antigen at a lower concentration or to bind an additional antigen, wherein this process can continue for two or more cycles, wherein the antibody or antibodies that bind on the last cycle are selected.

Herein the term "screening" refers to a method of isolating an antibody or antibodies from other antibodies, based on the level of binding activity to an antigen. An example of a screening method is a phage ELISA.

Herein the term "selecting" refers to a method of isolating an antibody or antibodies from other antibodies based on the ability to bind an antigen.

In view of the foregoing, the present invention provides an isolated or purified nucleic acid molecule comprising the nucleotide sequence encoding the amino acid sequence of SEQ ID NO: 1, SEQ ID NO: 2, SEQ ID NO: 8 or a variant of any of the foregoing, wherein the variant retains the ability to bind to the same epitope as that of SEQ ID NO: 1, 2 or 8, respectively, to a greater or lesser extent.

The term "isolated" as used herein means having been removed from its natural environment. The term "purified" as used herein means having been increased in purity, wherein "purity" is a relative term, and not to be construed as absolute purity. The term "nucleic acid molecule" as used herein means a polymer of DNA or RNA, (i.e., a polynucleotide), which can be single-stranded or double-stranded, synthesized or obtained from natural sources, and which can contain natural, non-natural or altered nucleotides. Such nucleic acid molecules can be synthesized in accordance with methods well-known in the art.

The nucleic acid molecule encoding a variant can comprise one or more mutations. By "mutation" is meant any insertion, deletion, substitution and/or inversion in a given oligonucleotide. Such mutated oligonucleotides and fragments thereof can be obtained from naturally occurring sources or generated using methods known in the art. For instance, site-specific mutations can be introduced by ligating into an expression vector a synthesized oligonucleotide comprising the mutation(s). Alternately, oligonucleotide-directed site-specific mutagenesis procedures can be used, such as disclosed in Walder et al., Gene 42: 133 (1986); Bauer et al., Gene 37: 73 (1985); Craik, Biotechniques, 12-19 (January 1995); and U.S. Pat. Nos. 4,518,584 and 4,737,462. A preferred means for introducing mutations is the QuikChange Site-Directed Mutagenesis Kit (Stratagene, LaJolla, Calif.). While the above-described mutated oligonucleotides and fragments thereof can be generated in vivo and then isolated or purified, alternatively, they can be synthesized. A variety of techniques used to synthesize the oligonucleotides and fragments thereof of the present invention are known in the art. See, for example, Lemaitre et al., *Proceedings of the National Academy of the Sciences* 84: 648-652 (1987) and the references cited herein under "EXAMPLES." The oligonucleotides and fragments thereof of the present invention can alternatively be synthesized by companies, such as Eurogentec, Belgium. Preferably, the nucleotides encoding CDRH3 remain unchanged or are only slightly changed, such as by conservative or neutral amino acid substitution(s) (see, e.g., FIGS. 2 and 3). Mutations can be tolerated elsewhere. Activity of the encoded antibody can be assess in vitro under physiological conditions.

A vector comprising any of the above-described isolated or purified nucleic acid molecules, or fragments thereof, is further provided by the present invention. Any of the above nucleic acid molecules, or fragments thereof, can be cloned into any suitable vector and can be used to transform or transfect any suitable host. The selection of vectors and methods to construct them are commonly known to persons of ordinary skill in the art and are described in general technical references (see, in general, "Recombinant DNA Part D," *Methods in Enzymology, Vol.* 153, Wu and Grossman, eds., Academic Press (1987)). Desirably, the vector comprises regulatory sequences, such as transcription and translation initiation and termination codons, which are specific to the type of host (e.g., bacterium, fungus, plant or animal) into which the vector is to be introduced, as appropriate and taking into consideration whether the vector is DNA or RNA. Preferably, the vector comprises regulatory sequences that are specific to the genus of the host. Most preferably, the vector comprises regulatory sequences that are specific to the species of the host.

Constructs of vectors, which are circular or linear, can be prepared to contain an entire nucleic acid sequence as described above or a portion thereof ligated to a replication system functional in a prokaryotic or eukaryotic host cell. Replication systems can be derived from ColE1, 2 mµ plasmid, λ, SV40, bovine papilloma virus, and the like.

In addition to the replication system and the inserted nucleic acid, the construct can include one or more marker genes, which allow for selection of transformed or transfected hosts. Marker genes include biocide resistance, e.g., resistance to antibiotics, heavy metals, etc., complementation in an auxotrophic host to provide prototrophy, and the like.

Suitable vectors include those designed for propagation and expansion or for expression or both. A preferred cloning vector is selected from the group consisting of the pUC series, the pBluescript series (Stratagene, LaJolla, Calif.), the pET series (Novagen, Madison, Wis.), the pGEX series (Pharmacia Biotech, Uppsala, Sweden), and the pEX series (Clontech, Palo Alto, Calif.). Bacteriophage vectors, such as λGT10, λGT11, λZapII (Stratagene), λ EMBL4, and λ NM1149, also can be used. Examples of plant expression vectors include pBI101, pBI101.2, pBI101.3, pBI121 and pBIN19 (Clontech). Examples of animal expression vectors include pEUK-C1, pMAM and pMAMneo (Clontech). The TOPO cloning system (Invitrogen, Carlsbad, Calif.) also can be used in accordance with the manufacturer's recommendations.

An expression vector can comprise a native or normative promoter operably linked to an isolated or purified nucleic acid molecule as described above. The selection of promoters, e.g., strong, weak, inducible, tissue-specific and developmental-specific, is within the skill in the art. Similarly, the combining of a nucleic acid molecule, or fragment thereof, as described above with a promoter is also within the skill in the art.

Suitable viral vectors include, for example, retroviral vectors, parvovirus-based vectors, e.g., adeno-associated virus (AAV)-based vectors, AAV-adenoviral chimeric vectors, and adenovirus-based vectors, and lentiviral vectors, such as Herpes simplex (HSV)-based vectors. These viral vectors can be prepared using standard recombinant DNA techniques described in, for example, Sambrook et al., *Molecular Cloning, a Laboratory Manual*, 2d edition, Cold Spring Harbor Press, Cold Spring Harbor, N.Y. (1989); and Ausubel et al., *Current Protocols in Molecular Biology*, Geene Publishing Associates and John Wiley & Sons, New York, N.Y. (1994).

A retroviral vector is derived from a retrovirus. Retrovirus is an RNA virus capable of infecting a wide variety of host cells. Upon infection, the retroviral genome integrates into the genome of its host cell and is replicated along with host cell DNA, thereby constantly producing viral RNA and any nucleic acid sequence incorporated into the retroviral genome. As such, long-term expression of a therapeutic factor(s) is achievable when using retrovirus. Retroviruses contemplated for use in gene therapy are relatively non-pathogenic, although pathogenic retroviruses exist. When employing pathogenic retroviruses, e.g., human immunodeficiency virus (HIV) or human T-cell lymphotrophic viruses (HTLV), care must be taken in altering the viral genome to eliminate toxicity to the host. A retroviral vector additionally can be manipulated to render the virus replication-deficient. As such, retroviral vectors are considered particularly useful for stable gene transfer in vivo. Lentiviral vectors, such as HIV-based vectors, are exemplary of retroviral vectors used for gene delivery. Unlike other retroviruses, HIV-based vectors are known to incorporate their passenger genes into non-dividing cells and, therefore, can be of use in treating persistent forms of disease.

AAV vectors are viral vectors of particular interest for use in gene therapy protocols. AAV is a DNA virus, which is not known to cause human disease. The AAV genome is comprised of two genes, rep and cap, flanked by inverted terminal repeats (ITRs), which contain recognition signals for DNA replication and packaging of the virus. AAV requires co-infection with a helper virus (i.e., an adenovirus or a Herpes simplex virus), or expression of helper genes, for efficient replication. AAV can be propagated in a wide array of host cells including human, simian, and rodent cells, depending on the helper virus employed. An AAV vector used for administration of a nucleic acid sequence typically has approximately 96% of the parental genome deleted, such that only the ITRs remain. This eliminates immunologic or toxic side effects due to expression of viral genes. If desired, the AAV rep protein can be co-administered with the AAV vector to enable integration of the AAV vector into the host cell genome. Host cells comprising an integrated AAV genome show no change in cell growth or morphology (see, e.g., U.S. Pat. No. 4,797, 368). As such, prolonged expression of therapeutic factors from AAV vectors can be useful in treating persistent and chronic diseases.

Optionally, the isolated or purified nucleic acid molecule, or fragment thereof, upon linkage with another nucleic acid molecule, can encode a fusion protein. The generation of fusion proteins is within the ordinary skill in the art and can involve the use of restriction enzyme or recombinational cloning techniques (see, e.g., Gateway™ (Invitrogen)). See, also, U.S. Pat. No. 5,314,995.

In view of the foregoing, the present invention also provides a composition comprising an above-described isolated or purified nucleic acid molecule, optionally in the form of a vector. The composition can comprise other components as described further herein.

Also in view of the above, the present invention provides a host cell comprising an above-described isolated or purified nucleic acid molecule, optionally in the form of a vector. It is most preferable that the cell of the present invention expresses the vector, such that the oligonucleotide, or fragment thereof, is both transcribed and translated efficiently by the cell. Examples of cells include, but are not limited to, a human cell, a human cell line, *E. coli* (e.g., *E. coli* TB-1, TG-2, DH5α, XL-Blue MRF' (Stratagene), SA2821 and Y1090), *B. subtilis, P. aerugenosa, S. cerevisiae, N. crassa*, insect cells (e.g., Sf9, Ea4) and others set forth herein below. The host cell can be present in a host, which can be an animal, such as a mammal, in particular a human.

An antibody to human immunodeficiency virus (HIV) envelope glycoprotein that can recognize one or more strains of HIV, wherein the epitope of HIV recognized by the antibody is inducible, and wherein the antibody binding to the epitope is enhanced by the presence of CD4 and the HIV co-receptor, e.g., CXCR4 or CCR5, is also provided by the present invention. Preferably, the antibody is a neutralizing scFv antibody or an Fab fragment. Preferably, the antibody can bind more than one clade of HIV. Preferably, the antibody comprises SEQ ID NO.: 1 or a variant thereof or SEQ ID NO: 2 or a variant thereof. Preferably, the variant retains the ability to bind to the same epitope as that of SEQ ID NO: 1 or 2, respectively, to a greater or lesser extent. While variants can be isolated from naturally occurring sources or be recombinantly produced, such variants also can be synthesized using standard peptide synthesizing techniques well-known to those of ordinary skill in the art (e.g., as summarized in Bodanszky, *Principles of Peptide Synthesis*, (Springer-Verlag, Heidelberg: 1984)). In particular, the polypeptide can be synthesized using the procedure of solid-phase synthesis (see, e.g., Merrifield, J. Am. Chem. Soc. 85: 2149-54 (1963); Barany et al., Int. J. Peptide Protein Res. 30: 705-739 (1987); and U.S. Pat. No. 5,424,398). If desired, this can be done using an automated peptide synthesizer. Removal of the t-butyloxycarbonyl (t-BOC) or 9-fluorenylmethyloxycarbonyl (Fmoc) amino acid blocking groups and separation of the polypeptide from the resin can be accomplished by, for example, acid treatment at reduced temperature. The polypeptide-containing mixture can then be extracted, for instance, with dimethyl ether, to remove non-peptidic organic compounds, and the synthesized polypeptide can be extracted from the resin powder (e.g., with about 25% w/v acetic acid). Following the synthesis of the polypeptide, further purification (e.g., using high performance liquid chromatography (HPLC)) optionally can be done in order to eliminate any incomplete polypeptides or free amino acids. Amino acid and/or HPLC analysis can be performed on the synthesized polypeptide to validate its identity. For other applications according to the invention, it may be preferable to produce the polypeptide as part of a larger fusion protein, such as by the methods described herein or other genetic means, or as part of a larger conjugate, such as through physical or chemical conjugation, as known to those of ordinary skill in the art and described herein.

The term "antibodies" is used herein in a broad sense and includes both polyclonal and monoclonal antibodies. In addition to intact immunoglobulin molecules, also included in the term "antibodies" are fragments or polymers of those immunoglobulin molecules, and human or humanized versions of immunoglobulin molecules or fragments thereof, as long as they are chosen for their ability to interact with the proteins disclosed herein. The antibodies can be tested for their desired activity using the in vitro assays described herein, or by analogous methods, after which their in vivo therapeutic and/or prophylactic activities are tested according to known clinical testing methods.

The term "monoclonal antibody" as used herein refers to an antibody obtained from a substantially homogeneous population of antibodies, i.e., the individual antibodies within the population are identical except for possible naturally occurring mutations that may be present in a small subset of the antibody molecules. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, as long as they exhibit the desired antagonistic activity (See, U.S. Pat. No. 4,816,567; and Morrison et al., *Proc. Natl. Acad. Sci. USA* 81: 6851-6855 (1984)).

The present inventive monoclonal antibodies can be made using any procedure which produces monoclonal antibodies. For example, monoclonal antibodies of the invention can be prepared using hybridoma methods, such as those described by Kohler and Milstein, *Nature,* 256:495 (1975). In a hybridoma method, a mouse or other appropriate host animal is typically immunized with an immunizing agent to elicit lymphocytes that produce antibodies that will specifically bind to the immunizing agent.

The monoclonal antibodies also can be made by recombinant DNA methods, such as those described in U.S. Pat. No. 4,816,567 (Cabilly et al.). DNA encoding the disclosed monoclonal antibodies can be readily isolated and sequenced using conventional procedures (e.g., by using oligonucleotide probes that are capable of binding specifically to genes encoding the heavy and light chains of antibodies). Libraries of antibodies or active antibody fragments also can be generated and screened using phage display techniques, e.g., as described in U.S. Pat. No. 5,804,440 to Burton et al. and U.S. Pat. No. 6,096,551 to Barbas et al.

In vitro methods are also suitable for preparing monovalent antibodies. Digestion of antibodies to produce fragments thereof, particularly, Fab fragments, can be accomplished using routine techniques known in the art. For instance, digestion can be performed using papain. Examples of papain digestion are described in International Patent Application Publication No. WO 94/29348, published Dec. 22, 1994, and U.S. Pat. No. 4,342,566. Papain digestion of antibodies typically produces two identical antigen binding fragments, called Fab fragments, each with a single antigen binding site, and a residual Fc fragment. Pepsin treatment yields a fragment that has two antigen combining sites and is still capable of cross-linking antigen.

As used herein, the term "antibody or fragments thereof" encompasses chimeric antibodies and hybrid antibodies, with dual or multiple antigen or epitope specificities, single chain antibodies and fragments, such as F(ab')2, Fab', Fab, scFv and the like, including hybrid fragments. Thus, fragments of the antibodies that retain the ability to bind their specific antigens are provided. For example, fragments of antibodies which maintain HIV gp120 binding activity are included within the meaning of the term "antibody or fragment thereof." Such antibodies and fragments can be made by techniques known in the art and can be screened for specificity and activity according to the methods set forth in the Examples and in general methods for producing antibodies and screening antibodies for specificity and activity (See Harlow and Lane. Antibodies, A Laboratory Manual. Cold Spring Harbor Publications, New York (1988)). Also included within the meaning of "antibody or fragments thereof" are conjugates of antibody fragments and antigen binding proteins (single chain antibodies) as described, for example, in U.S. Pat. No. 4,704,692, the contents of which are hereby incorporated by reference.

The fragments, whether attached to other sequences or not, can also include insertions, deletions, substitutions, or other selected modifications of particular regions or specific amino acids residues, provided the activity of the antibody or antibody fragment is not significantly altered or impaired compared to the non-modified antibody or antibody fragment. These modifications can provide for some additional property, such as to remove/add amino acids capable of disulfide bonding, to increase bio-longevity, to alter secretory characteristics; etc. In any case, the antibody or antibody fragment must possess a bioactive property, such as specific binding to its cognate antigen. Functional or active regions of the antibody or antibody fragment can be identified by mutagenesis of a specific region of the protein, followed by expression and testing of the expressed polypeptide. Such methods are readily apparent to a skilled practitioner in the art and can include site-specific mutagenesis of the nucleic acid encoding the antibody or antibody fragment (Zoller, M. J. *Curr. Opin. Biotechnol.* 3: 348-354 (1992)).

As used herein, the term "antibody" or "antibodies" can also refer to a human antibody and/or a humanized antibody. Many non-human antibodies (e.g., those derived from mice, rats, or rabbits) are naturally antigenic in humans, and thus can give rise to undesirable immune responses when administered to humans. Therefore, the use of human or humanized antibodies in the methods of the invention serves to lessen the chance that an antibody administered to a human will evoke an undesirable immune response.

Human antibodies also can be prepared using any other technique. Examples of techniques for human monoclonal antibody production include those described by Cole et al. (*Monoclonal Antibodies and Cancer Therapy*, Alan R. Liss, p. 77 (1985)) and by Boerner et al. (*J. Immunol.* 147(1): 86-95 (1991)). Human antibodies (and fragments thereof) also can be produced using phage display libraries (Hoogenboom et al., *J. Mol. Biol.* 227: 381 (1991); Marks et al., *J. Mol. Biol.* 222: 581 (1991)).

Human antibodies also can be obtained from transgenic animals. For example, transgenic, mutant mice that can produce a full repertoire of human antibodies in response to immunization have been described (see, e.g., Jakobovits et al., *Proc. Natl. Acad. Sci. USA* 90: 2551-255 (1993); Jakobovits et al., *Nature* 362: 255-258 (1993); and Bruggermann et al., *Year in Immunol.* 7: 33 (1993)). Specifically, the homozygous deletion of the antibody heavy chain joining region (J(H)) gene in these chimeric and germ-line mutant mice results in complete inhibition of endogenous antibody production, and the successful transfer of the human germ-line antibody gene array into such germ-line mutant mice results in the production of human antibodies upon antigen challenge.

Antibody humanization techniques generally involve the use of recombinant DNA technology to manipulate the DNA sequence encoding one or more polypeptide chains of an antibody molecule. Accordingly, a humanized form of a non-human antibody (or a fragment thereof) is a chimeric antibody or antibody chain (or a fragment thereof, such as an Fv, Fab, Fab', or other antigen-binding portion of an antibody) which contains a portion of an antigen binding site from a non-human (donor) antibody integrated into the framework of a human (recipient) antibody.

To generate a humanized antibody, residues from one or more complementarity determining regions (CDRs) of a recipient (human) antibody molecule are replaced by residues from one or more CDRs of a donor (non-human) antibody molecule that is known to have desired antigen binding characteristics (e.g., a certain level of specificity and affinity for the target antigen). In some instances, Fv framework (FR) residues of the human antibody are replaced by corresponding non-human residues. Humanized antibodies may also contain residues which are found neither in the recipient antibody nor in the imported CDR or framework sequences. Generally, a humanized antibody has one or more amino acid residues introduced into it from a source which is non-human. In practice, humanized antibodies are typically human antibodies in which some CDR residues and possibly some FR residues are substituted by residues from analogous sites in rodent antibodies. Humanized antibodies generally contain at least a portion of an antibody constant region (Fc), typically that of a human antibody (Jones et al., Nature 321: 522-525 (1986); Reichmann et al., Nature 332: 323-327 (1988); and Presta, Curr. Opin. Struct. Biol. 2: 593-596 (1992)).

Methods for humanizing non-human antibodies are well-known in the art. For example, humanized antibodies can be generated according to the methods of Winter and co-workers (Jones et al., Nature 321: 522-525 (1986); Riechmann et al., Nature 332: 323-327 (1988); and Verhoeyen et al., Science 239: 1534-1536 (1988)), by substituting rodent CDRs or CDR sequences for the corresponding sequences of a human antibody. Methods that can be used to produce humanized antibodies are also described in U.S. Pat. No. 4,816,567 (Cabilly et al.), U.S. Pat. No. 5,565,332 (Hoogenboom et al.), U.S. Pat. No. 5,721,367 (Kay et al.), U.S. Pat. No. 5,837,243 (Deo et al.), U.S. Pat. No. 5,939,598 (Kucherlapati et al.), U.S. Pat. No. 6,130,364 (Jakobovits et al.), and U.S. Pat. No. 6,180,377 (Morgan et al.).

A fusion protein or conjugate (conjugate produced by chemical or physical means) comprising an above-described antibody is also provided. The fusion protein or conjugate can comprise an other antibody that binds to an epitope of HIV, such as an antibody to HIV envelope glycoprotein that can recognize one or more strains of HIV, wherein the epitope of HIV recognized by the antibody is inducible, and wherein the antibody binding to the epitope is enhanced by the presence of CD4 and the HIV co-receptor. The other antibody can be a neutralizing scFv antibody fragment or an Fab fragment. Alternatively, the fusion protein or conjugate can comprise CD4, in which case the fusion protein can comprise the amino acid sequence of SEQ ID NO: 7 or a variant thereof, wherein the variant retains the ability to bind to the same epitope as that of SEQ ID NO: 7 to a greater or lesser extent. As another alternative, the fusion protein or conjugate can comprise a toxin.

Toxins are poisonous substances produced by plants, animals, or microorganisms that, in sufficient dose, are often lethal. A preferred toxin is Pseudomonas toxin. Diphtheria toxin is a substance produced by Corynebacterium diphtheria, which can be used therapeutically. This toxin consists of an α subunit and a β subunit, which, under proper conditions, can be separated. Another example of a toxin is tetanus toxoid, which is produced by Clostridium tetani. Lectins are proteins, usually isolated from plant material, which bind to specific sugar moieties. Many lectins are also able to agglutinate cells and stimulate lymphocytes. However, ricin is a toxic lectin, which has been used immunotherapeutically. This is accomplished by binding the alpha-peptide chain of ricin, which is responsible for toxicity, to the antibody molecule to enable site-specific delivery of the toxic effect. Other therapeutic agents, which can be coupled to the antibodies, are known, or can be easily ascertained, by those of ordinary skill in the art.

Many peptide toxins have a generalized eukaryotic receptor binding domain; in these instances the toxin must be modified to prevent intoxication of cells not bearing the targeted receptor (e.g., to prevent intoxication of cells not bearing the "X" receptor but having a receptor for the unmodified toxin). Any such modifications must be made in a manner which preserves the cytotoxic functions of the molecule. Potentially useful toxins include, but are not limited to: cholera toxin, ricin, Shiga-like toxin (SLT-I, SLT-II, SLT-IIV), LT toxin, C3 toxin, Shiga toxin, pertussis toxin, tetanus toxin, Pseudomonas exotoxin, alorin, saporin, modeccin, and gelanin. Diphtheria toxin can be used to produce molecules useful as described herein. Diphtheria toxin, whose sequence is known, and hybrid molecules thereof, are described in detail in U.S. Pat. No. 4,675,382 to Murphy. The natural diphtheria toxin molecule secreted by Corynebacterium diphtheriae consists of several functional domains which can be characterized, starting at the amino terminal end of the molecule, as enzymatically-active Fragment A (amino acids Gly1-Arg193) and Fragment B (amino acids Ser194-Ser535), which includes a translocation domain and a generalized cell binding domain (amino acid residues 475 through 535). The process by which diphtheria toxin intoxicates sensitive eukaryotic cells involves at least the following steps: (i) the binding domain of diphtheria toxin binds to specific receptors on the surface of a sensitive cell; (ii) while bound to its receptor, the toxin molecule is internalized into an endocytic vesicle; (iii) either prior to internalization, or within the endocytic vesicle, the toxin molecule undergoes a proteolytic cleavage between fragments A and B; (iv) as the pH of the endocytic vesicle decreases to below 6, the toxin crosses the endosomal membrane, facilitating the delivery of Fragment A into the cytosol; (v) the catalytic activity of Fragment A (i.e., the nicotinamide adenine dinucleotide-dependent adenosine diphosphate (ADP) ribosylation of the eukaryotic protein synthesis factor termed "Elongation Factor 2") causes the death of the intoxicated cell. A single molecule of Fragment A introduced into the cytosol is sufficient to inhibit the cell's protein synthesis machinery and kill the cell. The mechanism of cell killing by Pseudomonas exotoxin A, and possibly by certain other naturally-occurring toxins, is very similar.

A mixed toxin molecule is a molecule derived from two different polypeptide toxins. Generally, as discussed above in connection with diphtheria toxin, polypeptide toxins have, in addition to the domain responsible for generalized eukaryotic cell binding, an enzymatically active domain and a translocation domain. The binding and translocation domains are required for cell recognition and toxin entry respectively. Naturally-occurring proteins which are known to have a translocation domain include diphtheria toxin, Pseudomonas exotoxin A, and possibly other peptide toxins. The translocation domains of diphtheria toxin and Pseudomonas exotoxin A are well characterized (see, e.g., Hoch et al., Proc. Natl. Acad. Sci. USA 82:1692, 1985; Colombatti et al., J. Biol. Chem. 261: 3030 (1986); and Deleers et al., FEBS Lett. 160: 82 (1983)), and the existence and location of such a domain in other molecules may be determined by methods such as those employed by Hwang et al. (Cell 48:129 (1987)); and Gray et al. (PNAS USA 81: 2645 (1984)). A useful mixed toxin hybrid molecule can be formed by fusing the enzymatically active A subunit of E. coli Shiga-like toxin (Calderwood et al., PNAS USA 84: 4364 (1987)) to the translocation domain (amino acid residues 202 through 460) of diphtheria toxin, and to a molecule targeting a particular cell type, as described in U.S.

Pat. No. 5,906,820 to Bacha. The targeting portion of the three-part hybrid causes the molecule to attach specifically to the targeted cells, and the diphtheria toxin translocation portion acts to insert the enzymatically active A subunit of the Shiga-like toxin into the targeted cell. The enzymatically active portion of Shiga-like toxin, like diphtheria toxin, acts on the protein synthesis machinery of the cell to prevent protein synthesis, thus killing the cell.

The targeting molecule (for example, the antibody), and the cytotoxin can be linked in several ways. If the hybrid molecule is produced by expression of a fused gene, a peptide bond serves as the link between the cytotoxin and the antibody or antibody fragment. Alternatively, the toxin and the binding ligand can be produced separately and later coupled by means of a non-peptide covalent bond. For example, the covalent linkage may take the form of a disulfide bond. In this case, the DNA encoding the antibody can be engineered to contain an extra cysteine codon. The cysteine must be positioned so as to not interfere with the binding activity of the molecule. The toxin molecule must be derivatized with a sulfhydryl group reactive with the cysteine of the modified antibody. In the case of a peptide toxin this can be accomplished by inserting a cysteine codon into the DNA sequence encoding the toxin. Alternatively, a sulfhydryl group, either by itself or as part of a cysteine residue, can be introduced using solid phase polypeptide techniques. For example, the introduction of sulfhydryl groups into peptides is described by Hiskey (*Peptides* 3: 137 (1981)). The introduction of sulfhydryl groups into proteins is described in Maasen et al. (*Eur. J. Biochem.* 134: 32 (1983)). Once the correct sulfhydryl groups are present, the cytotoxin and antibody are purified, both sulfur groups are reduced; cytotoxin and ligand are mixed; (in a ratio of about 1:5 to 1:20) and disulfide bond formation is allowed to proceed to completion (generally 20 to 30 minutes) at room temperature. The mixture is then dialyzed against phosphate buffered saline or chromatographed in a resin such as Sephadex to remove unreacted ligand and toxin molecules.

Numerous types of cytotoxic compounds can be joined to proteins through the use of a reactive group on the cytotoxic compound or through the use of a cross-linking agent. A common reactive group that will form a stable covalent bond in vivo with an amine is isothiocyanate (Means et al., *Chemical Modifications of Proteins*, Holden-Day, San Francisco (1971), pp. 105-110). This group preferentially reacts with the ε-amine group of lysine. Maleimide is a commonly used reactive group to form a stable in vivo covalent bond with the sulfhydryl group on cysteine (Ji, *Methods Enzymol.* 91: 580-609 (1983)). Monoclonal antibodies are incapable of forming covalent bonds with radiometal ions, but they can be attached to the antibody indirectly through the use of chelating agents that are covalently linked to the antibodies. Chelating agents can be attached through amines (Meares et al., *Anal Biochem.* 142: 68-78 (1984)) and sulfhydryl groups (Koyama, *Chem. Abstr.* 120: 217262t (1994)) of amino acid residues and also through carbohydrate groups (Rodwell et al., *Proc. Natl. Acad. Sci.* 83: 2632-2636 (1986); Quadri et al., *Nucl. Med. Biol.* 20: 559-570 (1993)). Since these chelating agents contain two types of functional groups, one to bind metal ions and the other to joining the chelate to the antibody, they are commonly referred as bifunctional chelating agents (Sundberg et al., *Nature* 250: 587-588 (1974)).

Crosslinking agents have two reactive functional groups and are classified as being homo or heterobifunctional. Examples of homobifunctional crosslinking agents include bismaleimidohexane (BMH), which is reactive with sulfhydryl groups (Chen et al., *J. Biol. Chem.* 266: 18237-18243 (1991)), and ethylene glycolbis[succinimidylsucciate] (EGS), which is reactive with amino groups (Browning et al., *J. Immunol.* 143: 1859-1867 (1989)). An example of a heterobifunctional crosslinker is m-maleimidobenzoyl-N-hydroxysuccinimide ester (MBS) (Myers et al., *J. Immunol. Meth.* 121: 129-142 (1989)). These methodologies are simple and are commonly employed.

The above nucleic acid molecules, vectors, host cells, antibodies, fusion proteins and conjugtes are preferably administered to a subject as a composition, such as one comprising a pharmaceutically acceptable carrier. By "pharmaceutically acceptable" is meant a material that is not biologically or otherwise undesirable, i.e., the material can be administered to a subject without causing any undesirable biological effects or interacting in a deleterious manner with any of the other components of the pharmaceutical composition in which it is contained. The carrier is selected to minimize any degradation of the active ingredient and to minimize any adverse side effects in the subject. Suitable carriers and their formulations are described in *Remington: The Science and Practice of Pharmacy* (19th ed.), A. R. Gennaro, ed., Mack Publishing Company, Easton, Pa. (1995), and include carriers, thickeners, diluents, buffers, preservatives, surface-active agents, and the like, in addition to the active agent. The pharmaceutical composition also can comprise one or more active ingredients, such as antimicrobial agents, anti-inflammatory agents, anesthetics, and the like. Typically, an appropriate amount of a pharmaceutically acceptable salt is used in the formulation to render the formulation isotonic. Examples of pharmaceutically acceptable carriers include, but are not limited to, saline, Ringer's solution and dextrose solution. The pH of the solution is preferably from about 5 to about 8, and more preferably from about 7 to about 7.5. Further carriers include sustained-release preparations, such as semipermeable matrices of solid hydrophobic polymers containing the antibody, which matrices are in the form of shaped articles, e.g., films, liposomes or microparticles. It will be apparent to those persons skilled in the art that certain carriers can be preferable depending upon, for instance, the route of administration and concentration of antibody being administered.

The above nucleic acid molecules, vectors, host cells, antibodies, fusion proteins and conjugates can be administered to a human or a collection of cells by injection (e.g., transdermal, intravenous, intraperitoneal, subcutaneous, intramuscular), or by other methods, such as infusion, that ensure delivery to the bloodstream in an effective form. Local or intravenous injection is preferred. Other methods include topical, such as topical intranasal administration or administration by inhalant, vaginal, rectal, ophthalmic, oral, intravenous drop, subcutaneous, and the like.

As used herein, "topical intranasal administration" means delivery of the compositions into the nose and nasal passages through one or both of the nares and can comprise delivery by a spraying mechanism or droplet mechanism, or through aerosolization. Delivery also can be directly to any area of the respiratory system (e.g., lungs) via intubation.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives also can be present such as, for example, antimicrobials, antioxidants, chelating agents, inert gases and the like.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves the use of a slow-release or sustained-release system such that a constant dosage is maintained. See, e.g., U.S. Pat. No. 3,610, 795, which is incorporated by reference herein.

The composition (for example, incorporated into microparticles, liposomes, or cells) can be targeted to a particular cell type via antibodies, receptors, or receptor ligands. The following references are examples of the use of this technology to target specific proteins to tumor tissue (Senter et al., *Bioconjugate Chem.* 2: 447-451 (1991); Bagshawe, *Br. J. Cancer* 60: 275-281 (1989); Bagshawe et al., *Br. J. Cancer* 58: 700-703 (1988); Senter et al., *Bioconjugate Chem.* 4:3-9 (1993); Battelli et al., *Cancer Immunol. Immunother.* 35: 421-425 (1992); Pietersz and McKenzie, *Immunolog. Reviews* 129: 57-80 (1992); and Roffler et al., *Biochem. Pharmacol* 42: 2062-2065 (1991)). Vehicles, such as "stealth" and other antibody-conjugated liposomes (including lipid-mediated drug targeting), receptor-mediated targeting of DNA through cell specific ligands, lymphocyte-directed tumor targeting, and highly specific therapeutic retroviral targeting of cells in vivo, can be used. The following references are examples of the use of this technology to target specific proteins to tissue (Hughes et al., *Cancer Research* 49: 6214-6220 (1989); and Litzinger and Huang, *Biochimica et Biophysica Acta* 1104: 179-187 (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis have been reviewed (Brown and Greene, *DNA and Cell Biology* 10(6): 399-409 (1991)).

Formulations for topical administration may include ointments, lotions, creams, gels, drops, suppositories, sprays, liquids and powders. Conventional pharmaceutical carriers, aqueous, powder or oily bases, thickeners and the like can be necessary or desirable.

Compositions for oral administration include powders or granules, suspensions or solutions in water or non-aqueous media, capsules, sachets, or tablets. Thickeners, flavorings, diluents, emulsifiers, dispersing aids or binders can be desirable. Some of the compositions potentially can be administered as a pharmaceutically acceptable acid- or base-addition salt, formed by reaction with inorganic acids, such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base, such as sodium hydroxide, ammonium hydroxide, and potassium hydroxide, and organic bases, such as mono-, di-, trialkyl and aryl amines and substituted ethanolamines.

Effective dosages and schedules for administering the above nucleic acid molecules, vectors, host cells, antibodies, and fusion proteins can be determined empirically, and making such determinations is within the skill in the art. Those skilled in the art will understand that the dosage that must be administered will vary depending on, for example, the subject, the route of administration, whether a nucleic acid molecule, vector, host cell, antibody, fusion protein or conjugate is being administered, and whether other drugs being administered, not to mention the age, condition, and gender of the human and the extent of disease. Guidance in selecting appropriate doses for antibodies (or fusion proteins comprising same) is found in the literature on therapeutic uses of antibodies, e.g., Handbook of Monoclonal Antibodies, Ferrone et al., eds., Noges Publications, Park Ridge, N.J. (1985), Ch. 22 and pp. 303-357; Smith et al., Antibodies in Human Diagnosis and Therapy, Haber et al., eds., Raven Press, New York (1977), pp. 365-389. A typical daily dosage of the antibody used alone can range from about 1 µg/kg up to about 100 mg/kg of body weight or more per day, depending on the factors mentioned above. For example, the range can be from about 100 mg to one gram per dose. Nucleic acids, vectors and host cells should be administered so as to result in comparable levels of production of antibodies or fusion proteins thereof.

Following administration of a nucleic acid molecule, vector, host cell, antibody, fusion protein or conjugate for treating, inhibiting, or reducing the severity of an HIV infection, the efficacy of the therapeutic agent can be assessed in various ways well-known to the skilled practitioner. For instance, one of ordinary skill in the art will understand that an antibody of the invention is efficacious in treating or inhibiting an HIV infection in a subject by observing that the antibody reduces viral load or prevents a further increase in viral load. Viral loads can be measured by methods that are known in the art, for example, using polymerase chain reaction assays to detect the presence of HIV nucleic acid or antibody assays to detect the presence of HIV protein in a sample (e.g., but not limited to, blood) from a subject or patient, or by measuring the level of circulating anti-HIV antibody levels in the patient. Efficacy of the antibody treatment also can be determined by measuring the number of $CD4^+$ T cells in the HIV-infected subject. An antibody treatment that inhibits an initial or further decrease in $CD4^+$ T cells in an HIV-positive subject or patient, or that results in an increase in the number of $CD4^+$ T cells in the HIV-positive subject, is an efficacious antibody treatment.

The nucleic acid molecules, vectors, host cells, antibodies, fusion proteins and/or conjugates of the invention can be administered prophylactically to patients or subjects who are at risk for being exposed to HIV or who have been newly exposed to HIV. In subjects who have been newly exposed to HIV but who have not yet displayed the presence of the virus (as measured by PCR or other assays for detecting the virus) in blood or other body fluid, efficacious treatment with an antibody of the invention partially or completely inhibits the appearance of the virus in the blood or other body fluid.

The nucleic acid molecules, vectors, host cells, antibodies, fusion proteins and/or conjugates of the invention can be combined with other well-known therapies and prophylactic vaccines already in use. Such combinations can generate an additive or a synergistic effect with current treatments. The nucleic acid molecules, vectors, host cells, antibodies and/or conjugates of the invention can be combined with HIV and AIDS therapies and vaccines such as highly active antiretroviral therapy (HAART), AZT, structured treatment interruptions of HAART, cytokine immune enhancement therapy (IL-2, IL-12, CD40L+ IL-12, IL-7, IFNs), cell replacement therapy, recombinant viral vector vaccines, DNA vaccines, inactivated virus preparations, and immunosuppressive agents, such as Cyclosporin A. Such therapies can be administered in the manner already in use for the known treatment providing a therapeutic or prophylactic effect (Silvestri and Feinberg "Immune Intervention in AIDS." In *Immunology of Infectious Disease*. H. E. Kauffman, A. Sher, and R. Ahmed eds., ASM Press. Washington D.C. (2002)).

As described above, the compositions can be administered in a pharmaceutically acceptable carrier and can be delivered to the subject's cells in vivo and/or ex vivo by a variety of mechanisms well-known in the art (e.g., uptake of naked DNA, liposome fusion, intramuscular injection of DNA via a gene gun, endocytosis and the like).

If ex vivo methods are employed, cells or tissues can be removed and maintained outside the body according to standard protocols well-known in the art. Compositions comprising a nucleic acid, optionally in the form of a vector encoding the antibody or fusion protein comprising same, can be introduced into the cells via any gene transfer mechanism, such as, for example, calcium phosphate mediated gene delivery, electroporation, microinjection or proteoliposomes. The transduced cells then can be infused (e.g., in a pharmaceutically acceptable carrier) or homotopically transplanted back into the subject per standard methods for the cell or tissue type. Standard methods are known for transplantation or infusion of various cells into a subject.

Thus, in view of the above, the present invention provides a method of inhibiting an infection of a human at risk of becoming infected with HIV. The method comprises administering to the human an infection-inhibiting amount of an above-described nucleic acid, vector, host cell, antibody or fusion protein, whereupon the infection of the human is inhibited. The HIV can be HIV-1 or HIV-2. One of ordinary skill in the art will appreciate that, in the context of HIV infection and AIDS, any degree of inhibition of infection can be beneficial. Preferably, the infection is inhibited to such a degree that the human does not evidence the signs and symptoms of infection and preferably does not develop AIDS.

Also in view of the above, the present invention provides a method of reducing the severity of an infection of a human infected with HIV, such as HIV-1 or HIV-2. The method comprises administering to the human a severity of infection-reducing amount of an above-described nucleic acid, vector, host cell, antibody or fusion protein, whereupon the severity of the infection of the human is reduced. One of ordinary skill in the art will appreciate that, in the context of HIV infection and AIDS, any degree of reduction in the severity of infection can be beneficial. Preferably, the reduction in the severity of infection is to such a degree that the human does not evidence the signs and symptoms of infection and preferably does not develop AIDS or, in the event that the human already has been diagnosed with AIDS, preferably the human does not experience an increase in the severity of AIDS.

Still also in view of the above, the present invention provides a method of treating an infection, such as a chronic infection, of a human with HIV, such as HIV-1 or HIV-2. The method comprises administering to the human an infection-treating amount of an above-described nucleic acid, vector, host cell, antibody or fusion protein, whereupon the infection of the human is treated. One of ordinary skill in the art will appreciate that, in the context of HIV infection and AIDS, any inhibition or amelioration of infection is beneficial. Preferably, the infection is treated to such a degree that the human does not evidence a worsening of the signs and symptoms of infection and preferably does not develop AIDS or, in the event that the human already has been diagnosed with AIDS, preferably the human does not experience an increase in the severity of AIDS. Also preferably, if the human is infected but has not yet developed AIDS, the human/s condition improves such that he/she becomes essentially asymptomatic and does not evidence signs of infection.

EXAMPLE

The following example serves to illustrate the present invention and is not intended to limit its scope in any way.

Selection of two phage scFvs (m6 and m9) with high affinity for different Env-CD4 complexes by SAP.

We hypothesized that, by sequential antigens during panning of phage display libraries and by screening the enriched libraries using different antigens, the selected phage will display scFvs against conserved epitopes shared among all antigens used during the entire selection process. Complexes of two different recombinant soluble Envs ($gp140_{89.6}$ and $gp140_{IIIB}$) with two-domain soluble CD4 (sCD4) were used as antigens for phage library panning as described in the Experimental Protocol. Screening of individual phage clones after panning was performed in phage ELISA with $gp140_{89.6}$, $gp120_{JR\text{-}FL}$, $gp140_{IIIB}$, and their complexes with sCD4. Two phage clones, designated m6 and m9, bound significantly to all antigens and were selected for her characterization. Phagemid DNA of m6 and m9 was prepared and sequenced. The two clones exhibited differences in the amino acid composition.

Binding of soluble Fab m6 and Fab m9 to gp120 and gp140 from different isolates is significantly increased by CD4.

m6 bound gp120 from the primary isolate 89.6 with a high affinity (nM), which was significantly increased after binding of sCD4 to gp120 as measured by an ELISA assay. Interestingly, although the affinity of m6 to gp120 alone was comparable to that of X5, the affinity to the 120-sCD4 was significantly increased.

Inhibition of Env-mediated Membrane Fusion.

To determine the breadth and potency of HIV neutralization by m6 we measured the ability to inhibit cell-cell fusion mediated by Envs of primary isolates from different clades in comparison with the potent broadly HIV neutralizing Fab X5 (Table 1). m6 inhibited cell-cell fusion mediated by Envs of primary isolates from different clades with a potency comparable (3 isolates), worse (2 isolates) or better (6 isolates) than X5 as measured by a cell fusion assay. These results suggest that m6 is a potent broadly HIV-1 neutralizing scFv antibody.

Experimental Protocol.

Construction of the X5 scFv Library.

The X5 scFv library was generated using standard approaches. Briefly, the X5 variable regions of heavy chain (VH) and light chain (VL) were amplified by PCR using two pairs of primer: VL5Sac and VL3Link for VL; VH5Link and VH3Spe for VH. X5 scFv resulted from SOE-PCR of VL and VH. PCR products were gel-purified, digested with Sac I and Spe I and gel-purified again. Purified fragment was then cloned to phagemid pComb3X linearized by Sac I and Spe I. To introduce point mutations to X5 scFv construct, we did DNA random mutagenesis with the GeneMorph PCR Mutagenesis Kit (Stratagene, La Jolla, Calif.) according to manufacture's instruction for high range mutation frequency with slight modification. The $1^{st}$ PCR reaction was carried out in a total volume of 50 μl by adding 10 pg of scFv DNA (60 pg of the recombinant phagemid DNA), 20 pmol of primer VL5Sac and VH3Spe and 2.5 units of mutazyme under the following conditions: an initial denaturation for 5 min at 94° C. followed by 30 cycles at 94° C. for 1 min, 55° C. for 1 min, 72° C. for 1 min and a filling cycle of 72° C. for 10 min. The $1^{st}$ PCR products were gel-purified and 25 ng of purified $1^{st}$ PCR products were used as templates in the $2^{nd}$ PCR amplification under the same conditions as described above. The products from the $2^{nd}$ PCR amplification were gel-purified and digested with Sac I and Spe I. The pComb3X containing the Fab X5 insert was digested with the same enzymes, and the resulting linearized vector was purified by agarose gel electrophoresis. The vector backbone was excised from the gel. The purified vector DNA was ligated with purified scFv fragments, and the ligation products were electroporated into electrocompetent E. coli XL1-blue cells to create an scFv mutagenesis library. Four separated ligations and transformations were pooled to increase the library diversity. The efficiency of this transformation with a total of 320 ng of purified scFv fragments yielded $1.2 \times 10^6$ independent transformants. Forty individual clones were randomly selected, and plasmid DNA was prepared and sequenced. The average mutation rate of 40 clones was 6 bases per kb DNA.

An scFv phage library was prepared from initial transformations upon infection with the replication-defective helper phage M13KO7. The phage titer was determined by the addition of dilutions to exponentially growing E. coli XL1-blue cells.

Sequential Antigen Panning of the scFv Mutagenesis Library.

Phage ($5 \times 10^{12}$ cfu/ml) were preabsorbed on streptavidin-M280-Dynabeads in PBS for 1 h at room temperature (RT) followed by depletion in an immunotube (Nunc, Denmark) coated with 10 µg/ml sCD4 for 1 h at 37° C. A depleted phage library was incubated with 50 nM biotinylated $gp140_{89.6}$ complexed with sCD4 in solution (molar ratio of $gp140_{89.6}$ to sCD4=1:1) for 2 h at RT with gentle agitation. Phage binding to biotinylated Env were separated from the phage library using streptavidin-M280-Dynabeads and a magnetic separator (Dynal). The beads were washed 20 times with 1 ml of PBS containing 0.1% Tween-20 and another 20 times with 1 ml of PBS. Bound phage were eluted by incubation at RT for 10 min with 1 ml of 100 mM TEA, followed by neutralization with 0.5 ml of 1 M, pH 7.5, Tris-HCl. Eluted phage were rescued by infection of E. coli TG1 cells, and a phage library was prepared for the next round of panning. For the $2^{nd}$ round of panning, 10 nM (2 nM for the $3^{rd}$ round) of biotinylated $gp140_{89.6}$ complexed with sCD4 (1:1 on molar level) was used as antigen. For the $4^{th}$ round of panning, 2 nM of biotinylated $gp140_{IIIB}$ complexed with sCD4 (1:1 on molar level) was used as antigen. After the $3^{rd}$ and $4^{th}$ rounds of panning, 20 individual clones were screened by phage ELISA for binding to $gp140_{89.6}$, $gp120_{JRFL}$, $gp140_{IIIB}$ and their complexes with sCD4 as follows. Single colonies were inoculated into 1 ml of 2×YT medium containing 100 µg/ml ampicillin and 2% glucose in 12-ml falcon tubes. The tubes were incubated overnight at 37° C./250 rpm. Ten µl of overnight culture from each tube were inoculated into 1 ml of 2×YT medium containing 100 µg/ml ampicillin, 2% glucose and about $4 \times 10^9$ cfu/ml of $M_{13}KO_7$ in 12-ml falcon tubes. The phage tubes were incubated at 37° C./250 rpm for 2 h and centrifuged at 4,000 rpm for 10 min at RT. The supernatant was removed and the cells were suspended in 1 ml of 2×YT medium with 100 µg/ml ampicillin and 50 µg/ml kanamycin.

The tubes were then incubated overnight at 30° C./250 rpm. After 16 h, the tubes were centrifuged at 4,000 rpm for 10 min at 4° C. The supernatant was used for phage ELISA.

Phage ELISA.

Phage ELISA was performed by using 96-well Nunc-Immuno™ Maxisorp™ surface plates (Nalge Nunc International, Denmark), which were coated overnight at 4° C. with 100 µl of gp120/140 (1 µg/ml in sodium bicarbonate buffer, pH 8.3) or gp120/140-sCD4 complex (100 µg/ml gp120/140 in PBS were premixed with an equal volume of 100 µg/ml sCD4). After incubation at RT for 30 min, the mixture was diluted to 1 µg/ml in PBS, and blocked in 100 µl of 4% non-fat dry milk in PBS for 1 hour at 37° C. After 4 washes with 0.05% Tween20/PBS washing buffer (WB), wells were incubated with 100 µl of phage supernatant for 2 hour at 37° C. Bound phage were detected by using horseradish peroxidase (HRP) conjugated anti-M13 monoclonal antibody (Pharmacia) with incubation for 1 h at 37° C. and revealed by adding ready-to-use ABTs substrate (Pharmacia). Color development was performed at RT for 15 min and monitored at 405 nm.

Preparation of Soluble scFv Fragments.

The pComb3X phagemids containing m6 and m9 scFv genes were prepared and transformed to E. coli Top 10. His 6-tagged soluble scFvs were expressed and purified by IMAC using Ni-NTA resin according to manufacturer's protocols.

Enzyme-linked Immunosorbent Assays (ELISAs).

ELISA was performed by using 96-well Nunc-Immuno™ Maxisorp™ surface plates. Coating of antigen and washing and blocking steps were the same as described for phage ELISA. For scFv binding assay, microplate wells were incubated with 100 µl two-fold serially diluted biotinylated soluble scFv for 2 hours at 37° C. After 4 washes with WB, 100 µl of a 1:2,500 dilution of HIP-streptavidin were added and incubated for 1 hour at 37° C. Following 4 washes with WB, the assay was developed at 37° C. for 15-30 minutes with ready-to-use ABTs substrate and monitored at 405 nm. For competition ELISA, 50 µl of two-fold serially diluted competing scFv hmAbs (m6, m9 or scFv X5) were added to the blocked and washed wells, immediately followed by addition of 50 µl of Fab or IgG hmAbs (X5, IgG 17b, IgG b12) previously determined to result in an ELISA signal that was 50 to 75% of maximum without competitor. After incubation for 2 h at 37° C., the wells were washed as above, probed with a HRP-conjugated anti-human IgG F(ab')$_2$ conjugate (Pierce) diluted 1:2,500 in PBS containing 2% non-fat dry milk and detected as above.

Cell-cell Fusion Assay.

Cells ($10^5$ 293 cells) transfected with plasmids encoding various Envs under the control of the T7 promoter and infected with recombinant vaccinia virus encoding the T7 polymerase gene, were preincubated with m6 or X5 at 50 µg/ml for 30 min at 37° C., and then mixed with $10^5$ CEM-CCR5 cells. The extent of cell fusion was quantified by counting the number of syncytia 12 h later. The data are shown on Table 1, in which the data are averages of duplicate samples and presented as % of fusion inhibition.

TABLE 1

Inhibition of cell fusion mediated by Envs from various clades by m6 and X5.

| Env | UG0 37.8 | RW0 20.5 | US7 15.6 | HT5 93.1 | US0 05.11 | 89.6 | NL 4-3 | BR0 25.9 | TH0 22.4 | BR0 19.4 | UG9 75.10 |
|---|---|---|---|---|---|---|---|---|---|---|---|
| Clade | A | A | B | B | B | B | B | C | EA | F/B | G |
| m6 | 66 | 56 | 27 | 50 | 83 | 98 | 100 | 57 | 72 | 37 | 48 |
| X5 | 34 | 45 | 56 | 27 | 72 | 93 | 83 | 71 | 43 | 37 | 19 |

Infectious Virus Neutralization Assay.

This HIV-1 neutralization assay is based on the use of infectious virus and a reporter-gene cell line BC-53. Primary HIV-1 isolates were either isolated from Institutional Review Board-approved CDC Studies or obtained from the NIH Research and Reference Reagent Program through the WHO collaborative network. The detailed characteristics of various isolates, including subtype determination based on the envelope region and coreceptor usage using GHOST cell lines has been previously described (15-17). Viral stocks were generated by infection of CD8 depleted normal human peripheral blood mononuclear cells as previously described (15, 16). Viral stocks were filtered through 0.22 μm filters, aliquoted and maintained at −70° C. prior to use. A reporter gene based viral replication assay was used to read out the viral replication (18). Briefly, JC53-BL, an HIV-1 indicator cell line derived from HeLa cells that express high levels of CD4, CXCR4 and CCR5, contains reporter cassettes for luciferase and β-galactosidase both driven by the HIV-1 LTR (a kind gift of Tranzyme Inc. Birmingham Ala.). These cassettes allow detection of HIV-1 infection (tat production) by measuring either luciferase activity with a luminometer or by counting blue foci after staining the cells with X-gal. The JC53-BL cells are maintained in c-DMEM, which is DMEM supplemented with 10% fetal calf serum (Hyclone), 2 mM glutamine (Gibco), 100 units per ml penicillin G, and 100 ug/ml streptomycin (Gibco). The viral titers are determined by adding serial dilutions of the virus stocks in C-DMEM media containing 40 μg/ml DEAE-dextran to 20,000 JC53-BL cells per well in duplicate in 96 well plates. Following a 48 hour incubation at 37° C. in a 5% $CO_2$ incubator, the cells are fixed and stained. Blue foci are counted using a standard light microscope, and the titers are expressed as infectious units or blue foci units per ml. From the infectious unit data, MOI values are determined for the inhibition assays.

The neutralizing activities of the antibodies in this assay were determined as follows. The JC53-BL cells were removed from T-150 flasks using 0.017M PBS, 0.1 mM EDTA at a pH of 7.4 approximately 18 hours prior to starting the inhibition assays and were plated at a density of 20,000 cells per well in white 96 well plates in 50 μl of C-DMEM. Viral stocks (MOI range of 0.009 to 0.65) were pre-incubated with different concentrations of the mAbs (final concentrations of 100-0.05 μg/ml) for 1 hour, prior to addition to the cells in media containing 40 μg/ml DEAE-dextran to give a final volume of 200 μl per well. The plates were incubated in a 37° C., 5% $CO_2$ incubator for 48 hour incubation, and luciferase activity was measured using the Steady-Glo Luciferase Assay System (Promega, Madison, Wis.) following the manufacturer's lysis protocol. The light intensity was measured using a Tecan luminometer with Magellan software (Tecan, Research Triangle Park, NC), and values were calculated as relative light units (RLU). Percent inhibition was calculated by the following formula 1−((average RLU of mAb containing wells/average RLU of virus only wells)×100=% inhibition. All assays were performed in duplicates and some in triplicates. The data are presented in Table 2.

TABLE 2

Neutralization of diverse HIV-1 isolates by m6, m9 and scFv X5.

| Virus[a] | Subtype gag/env | Core-ceptor | Inhibition (%) m6 50 ug/ml | m9 50 ug/ml | scFv X5 50 ug/ml |
|---|---|---|---|---|---|
| 92US714 | /B | R5 | 94 | 94 | 60 |
| 92US727 | /B | R5 | 22 | 24 | 73 |
| 92BR023 | C/B | R5 | 82 | 100 | 57 |
| 92HT593 | /B | R5X4 | 85 | 88 | 63 |
| 93US151 | /B | R5X4 | 100 | 100 | 69 |
| 92US076 | /B | R5X4 | 47 | 52 | 28 |
| 92UG031 | A/A | R5 | 76 | 79 | 29 |
| 92UG037 | A/A | R5 | 13 | 44 | 65 |
| 97USSN54 | A/A | R5 | 11 | 11 | 6 |
| 92RW024 | D/A | R5 | 45 | 74 | 42 |
| 92RW009 | C/A | R5X4 | 81 | 95 | 57 |
| 97ZA003 | C/C | R5 | 67 | 72 | 25 |
| 98CN006 | C/C | R5 | 92 | 96 | 34 |
| 98IN017 | /C | X4 | 91 | 93 | 30 |
| 92TH001 | A/E | R5 | 18 | 31 | 58 |
| 93TH073 | A/E | R5 | 46 | 31 | 23 |
| 93TH060 | A/E | R5 | 58 | 40 | 48 |
| HM16 | A/E | X4 | 100 | 96 | nd |
| HM14 | A/E | X4 | 81 | 45 | 52 |
| CMU 08 | A/E | R5X4 | 98 | 100 | 35 |
| 93BR019 | /BF | R5 | 50 | 29 | 66 |
| 93BR029 | B/F | R5 | 58 | 45 | 30 |
| 93BR020 | F/F | R5X4 | 39 | 19 | 25 |
| JV1083 | /G | R5 | 42 | 29 | 22 |
| HIV-G3 | /G | R5 | 53 | 63 | 14 |
| YBF-30 | Grp N | R5 | 71 | 85 | 14 |
| BCF-01 | Grp O | R5 | 10 | 0 | 0 |
| BCF-02 | Grp O | R5 | 32 | 7 | 46 |
| BCF-03 | Grp O | R5 | 0 | 0 | 3 |
| 5084/5-83§ | B | R5 | 70 | 85 | 53 |
| 5084/10-86AIDS§ | B | R5X4 | 71 | 87 | 18 |
| 5048/7-82§ | B | R5 | 51 | 83 | 0 |
| 5048/3-91AIDS§ | B | R5X4 | 96 | 100 | 45 |

[a]HIV-1 isolates. Their subtypes were determination based on the envelope region and coreceptor usage using GHOST cell lines (1-5). nd—not determined
§virus isolated from rapid progressor (5084) or late progressor (5048) witdates of isolations and disease status stated. Both patients had switch in their coreceptor usage over time.

Inhibition of Pseudovirus Entry Assay.

In this assay format single-round infectious molecular clones, produced by envelope complementation, were used. The degree of virus neutralization by antibody was achieved by measuring luciferase activity. Briefly, $2 \times 10^4$ U87.CD4.CCR5.CXCR4 cells in 100 μl of medium (DMEM containing 15% FBS, 1 μg of puromycin/ml, 300 μg of G418/ml, glutamine, and penicillin-streptomycin) were added to microplate wells (96-well flat-bottom; Corning Inc., Corning, N.Y.) and incubated for 24 h at 37° C. in 5% $CO_2$. One hundred microliters of medium containing an amount of virus previously determined to yield ~100,000 counts was mixed with various amounts of antibody, incubated for 1 h at 37° C., added to the cells, and incubated for a filter 3 days. The wells were aspirated and washed once with PBS, and 60 µl of luciferase cell culture lysis reagent (Promega, Madison, Wis.) were added. The wells were scraped and the lysate was mixed by pipetting, 50 µl were transferred to a round-bottom plate (Corning), and the plate was centrifuged at 1,800×g for 10 min at 4° C. Twenty microliters were transferred to an opaque assay plate (Corning), and the luciferase activity was measured on a luminometer (EG&G Berthold LB 96V; Perkin Elmer, Gaithersburg, Md.) by using luciferase assay reagent (Promega). The data are presented in Table 3.

TABLE 3

Neutralizing activity of m6, m9 and scFv X5 for selected HIV-1 isolates measured by an assay based on pseudovirus.

| Virus | m6 | | m9 | | scFv X5 | |
|---|---|---|---|---|---|---|
| | IC50 | IC90 | IC50 | IC90 | IC50 | IC90 |
| HxB2 | 1 | 6 | 1 | 5 | 1 | 7 |
| JRCSF | 5 | 30 | 3 | 15 | 5 | 30 |
| YU2 | 3 | 100 | 2 | 25 | 50 | >100 |
| 89.6 | 2 | 26 | 0.1 | 5 | 4 | 8 |

PBMC-Based Assay for Neutralization of Infectious HIV.

The PBMC-based neutralization assay was performed as follows. Serial two-fold dilutions of Abs in 50 µl were incubated with an equal volume of virus containing 100 TCID$_{50}$ for 1 h at 37° C. and added to 100 µl of PHA-activated PBMC ($5 \times 10^5$/ml). The calculated neutralization titers refer to the Ab concentration present during this incubation step. After overnight incubation, the cells were washed twice with tissue culture medium. On day 4, 100 µl of medium were replaced with fresh tissue culture medium. Triplicate samples were taken on days 4 and 7, treated with 1% Empigen (Calbiochem) and tested for p24 Ag content using an in-house ELISA. When the values for the p24 concentration at the day 7 were saturated, data for day 4 were used for analysis. The data are presented in Table 4.

TABLE 4

Standard p24 PBMC assay

IC90s in µg/ml

| Virus | IgG X5 | Fab X5 | scFv X5 | m6 | m9 |
|---|---|---|---|---|---|
| 89.6 | >300 | >100 | 12 | 18 | 6 |
| 93BR020 | >300 | >100 | >50 | >50 | 25 |
| Jrcsf | >300 | 100 | 12 | 8 | 4 |

The data are the average of two experiments done in triplicate.

Throughout this application, various publications are referenced. The disclosures of these publications in their entireties are hereby incorporated by reference into this application in order to more fully describe the state of the art to which this invention pertains. The references disclosed are also individually and specifically incorporated by reference herein for the material contained in them that is discussed in the sentence in which the reference is relied upon. If the number designation is not associated with a particular number it will be clear to one of skill which reference is being referred to by the context the reference is relied upon and by a review of the various possible references. The examples all refer to a particular set of references, and thus do not have a letter designation associated with individual numbers.

It will be apparent to those skilled in the art that various modifications and variations can be made in the present invention without departing from the scope or spirit of the invention. It will also be apparent to those skilled in the art that nucleic acid sequences are disclosed by the disclosure of the amino acid sequences as one skilled in the art will know what nucleic acids comprise an amino acid. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

REFERENCES

1. Dimitrov, Cell biology of virus entry. *Cell* 101: 697-702 (2000).
2. Chan et al., HIV entry and its inhibition. *Cell* 93: 681-684 (1998).
3. Sodroski, HIV-1 entry inhibitors in the side pocket. *Cell* 99: 243-246 (1999).
4. Dimitrov et al., A place for HIV-1 and T4 cells to meet. Identifying the coreceptor mediating HIV-1 entry raises new hopes in the treatment of AIDS. *Nature Medicine* 2: 640-641 (1996).
5. LaCasse et al., Fusion-competent vaccines: broad neutralization of primary isolates of HIV. *Science* 283: 357-362 (1999).
6. Moulard et al., Broadly cross-reactive HIV-1 neutralizing human monoclonal antibody selected for binding to gp120-CD4-CCR5 complexes. *PNAS USA*, 99(10): 6913-6918 (2002).
7. Burton et al., Efficient neutralization of primary isolates of HIV-1 by a recombinant human monoclonal antibody. *Science* 266: 1024-1027 (1994).
8. Muster et al., A conserved neutralizing epitope on gp41 of human immunodeficiency virus type 1. *J. Virol.* 67: 6642-6647 (1993).
9. Conley et al., Neutralization of divergent human immunodeficiency virus type 1 variants and primary isolates by IAM-41-2F5, an anti-gp41 human monoclonal antibody. *PNAS USA* 91: 3348-3352 (1994).
10. Trkola et al., Human monoclonal antibody 2G12 defines a distinctive neutralization epitope on the gp120 glycoprotein of human immunodeficiency virus type 1. *J. Virol.* 70: 1100-1108 (1996).
11. Zwick et al., Broadly Neutralizing Antibodies Targeted to the Membrane-Proximal External Region of Human Immunodeficiency Virus Type 1 Glycoprotein gp41. *J. Virol.* 75: 10892-10905 (2001).
12. Celada et al., Antibody raised against soluble CD4-rgp120 complex recognizes the CD4 moiety and blocks membrane fusion without inhibiting CD4-gp120 binding. *J. Exp. Med.* 172: 1143-1150 (1990).

13. Gershoni et al., HIV binding to its receptor creates specific epitopes for the CD4/gp120 complex. *FASEB J.* 7: 1185-7 (1993).

14. Kang et al., Immunization with a soluble CD4-gp120 complex preferentially induces neutralizing anti-human immunodeficiency virus type 1 antibodies directed to conformation-dependent epitopes of gp120. *J. Virol.* 68: 5854-5862 (1994).

15. Devico et al., Covalently crosslinked complexes of human immunodeficiency virus type 1 (HIV-1) gp120 and CD4 receptor elicit a neutralizing immune response that includes antibodies selective for primary virus isolates. *Virology* 218: 258-263 (1996).

16. Sullivan et al., CD4-Induced conformational changes in the human immunodeficiency virus type 1 gp120 glycoprotein: consequences for virus entry and neutralization. *J. Virol.* 72: 4694-4703 (1998).

17. Nussbaum et al., Fusogenic mechanisms of enveloped-virus glycoproteins analyzed by a novel recombinant vaccinia virus-based assay quantitating cell fusion-dependent reporter gene activation. *J. Virol.* 68: 5411-5422 (1994).

18. Barbas et al., Phage Display: A Laboratory Mannual. Cold Spring Harbor Laboratory Press, Cold Spring Harbor (2001).

What is claimed is:

1. An isolated or purified nucleic acid molecule comprising a nucleotide sequence encoding an antibody or antibody fragment to human immunodeficiency virus (HIV) envelope glycoprotein that binds with one or more strains of HIV, wherein the antibody or antibody fragment comprises the amino acid sequence of SEQ ID NO: 1, SEQ ID NO: 2, or a variant thereof that retains the complementarity determining regions (CDRs) of SEQ ID NO: 1 or SEQ ID NO: 2, respectively, and the ability to bind to the same epitope.

2. The nucleic acid molecule of claim 1, wherein the nucleic acid sequence encodes the amino acid sequence of SEQ ID NO: 8.

3. A vector comprising the nucleic acid molecule of claim 1.

4. A composition comprising the nucleic acid molecule of claim 1 and a carrier.

5. An isolated host cell comprising the nucleic acid molecule of claim 1.

6. The cell of claim 5, wherein the cell expresses the antibody or antibody fragment comprising the amino acid sequence of SEQ ID NO: 1, SEQ ID NO: 2, or a variant thereof that retains the CDRs of SEQ ID NO: 1 or SEQ ID NO: 2, respectively, and the ability to bind to the same epitope.

7. The cell of claim 5, wherein the cell expresses the antibody or antibody fragment comprising the amino acid sequence of SEQ ID NO: 1 or SEQ ID NO: 2.

8. A composition comprising the vector of claim 3 and a carrier.

9. An isolated host cell comprising the vector of claim 3.

10. The cell of claim 9, wherein the cell expresses the antibody or antibody fragment comprising the amino acid sequence of SEQ ID NO: 1, SEQ ID NO: 2, or a variant thereof that retains the CDRs of SEQ ID NO: 1 or SEQ ID NO: 2, respectively, and the ability to bind to the same epitope.

11. The cell of claim 9, wherein the cell expresses the antibody or antibody fragment comprising the amino acid sequence of SEQ ID NO: 1 or SEQ ID NO: 2.

12. The nucleic acid molecule of claim 1, wherein the antibody or antibody fragment comprises the amino acid sequence of SEQ ID NO: 1 or SEQ ID NO: 2.

13. The vector of claim 3, the antibody or antibody fragment comprises the amino acid sequence of SEQ ID NO: 1 or SEQ ID NO: 2.

* * * * *